US007955828B2

(12) United States Patent
Droux et al.

(10) Patent No.: US 7,955,828 B2
(45) Date of Patent: Jun. 7, 2011

(54) USE OF METHIONINE SYNTHASE INHIBITORS FOR THE TREATMENT OF FUNGAL DISEASES OF CROPS

(75) Inventors: Michel Droux, Tassin la Demi Lune (FR); Marc-Henri Lebrun, Lyons (FR)

(73) Assignee: Bayer Cropscience AG (DE)

( * ) Notice: Subject to any disclaimer, the term of this patent is extended or adjusted under 35 U.S.C. 154(b) by 0 days.

(21) Appl. No.: 11/793,255

(22) PCT Filed: Dec. 20, 2005

(86) PCT No.: PCT/EP2005/014209

§ 371 (c)(1), (2), (4) Date: Jun. 18, 2007

(87) PCT Pub. No.: WO2006/066974

PCT Pub. Date: Jun. 29, 2006

(65) Prior Publication Data

US 2008/0132586 A1 Jun. 5, 2008

(30) Foreign Application Priority Data

Dec. 21, 2004 (FR) ...................................... 04 13628

(51) Int. Cl.

| | |
|---|---|
| ***C12N 9/00*** | (2006.01) |
| ***C12N 9/02*** | (2006.01) |
| ***C12N 1/20*** | (2006.01) |
| ***C12N 15/00*** | (2006.01) |
| ***A01N 25/00*** | (2006.01) |
| ***C07H 21/04*** | (2006.01) |

(52) U.S. Cl. ..................... 435/183; 435/189; 435/252.3; 435/320.1; 514/789; 536/23.2

(58) Field of Classification Search ........................ None
See application file for complete search history.

(56) References Cited

FOREIGN PATENT DOCUMENTS

WO PCT/US2004/191849 9/2004

OTHER PUBLICATIONS

Pacson et al. Microbiology. Sep. 2004;150(Pt 9):3013-23.*

Pascon, Renata C. et al.: "Cryptococcus Neoformans Methionine Synthase: Expression Analysis and Requirement for Virulence" Microbiology (Reading), vol. 150, No. Part 9, Sep. 2004, pp. 3013-3023, XP002346120, ISSN: 1350-0872.

Drummond, J. et al.: "Characterization of Nonradioactive Assays for Cobalamin-Dependent and Cobalamin-Independent Methionine Synthase Enzymes", Analytical Biochemistry, vol. 228, No. 2, 1995, pp. 323-329, XP002297999, ISSN: 0003-2697.

Huang, Longquan et al.: Assays of Methylenetetrahydrofolate Reductase and Methionine Synthase Activities by Monitoring 5-Methyltetrahydrofolate and Tetrahydorfolate Using High-Performance Liquid Chromatography with Fluorescence Detection, Analytical Biochemistry, vol. 299, No. 2, Dec. 15, 2001, pp. 253-259, XP002346121, ISSN: 0003-2697.

Solomon, Peter S. et al.: Methionine Synthase, A Gene Required for Methionine Synthesis, is Expressed in Planta by *Cladosporium fulvum*, Molecular Plant Pathology, vol. 1, No. 5, Sep. 2000, pp. 315, 323, XP002346122, ISSN: 1464-6722.

* cited by examiner

*Primary Examiner* — Christian L Fronda
(74) *Attorney, Agent, or Firm* — Ostrolenk Faber LLP

(57) ABSTRACT

The invention relates to the use of methionine synthase inhibitors for the treatment of fungal diseases of crops. The invention further relates to methods for treatment of crops against fungal diseases comprising the application of a methionine synthase inhibitor also methods for the identification of novel fungicidal compounds comprising a step for identification of methionine synthase inhibitors.

11 Claims, 1 Drawing Sheet

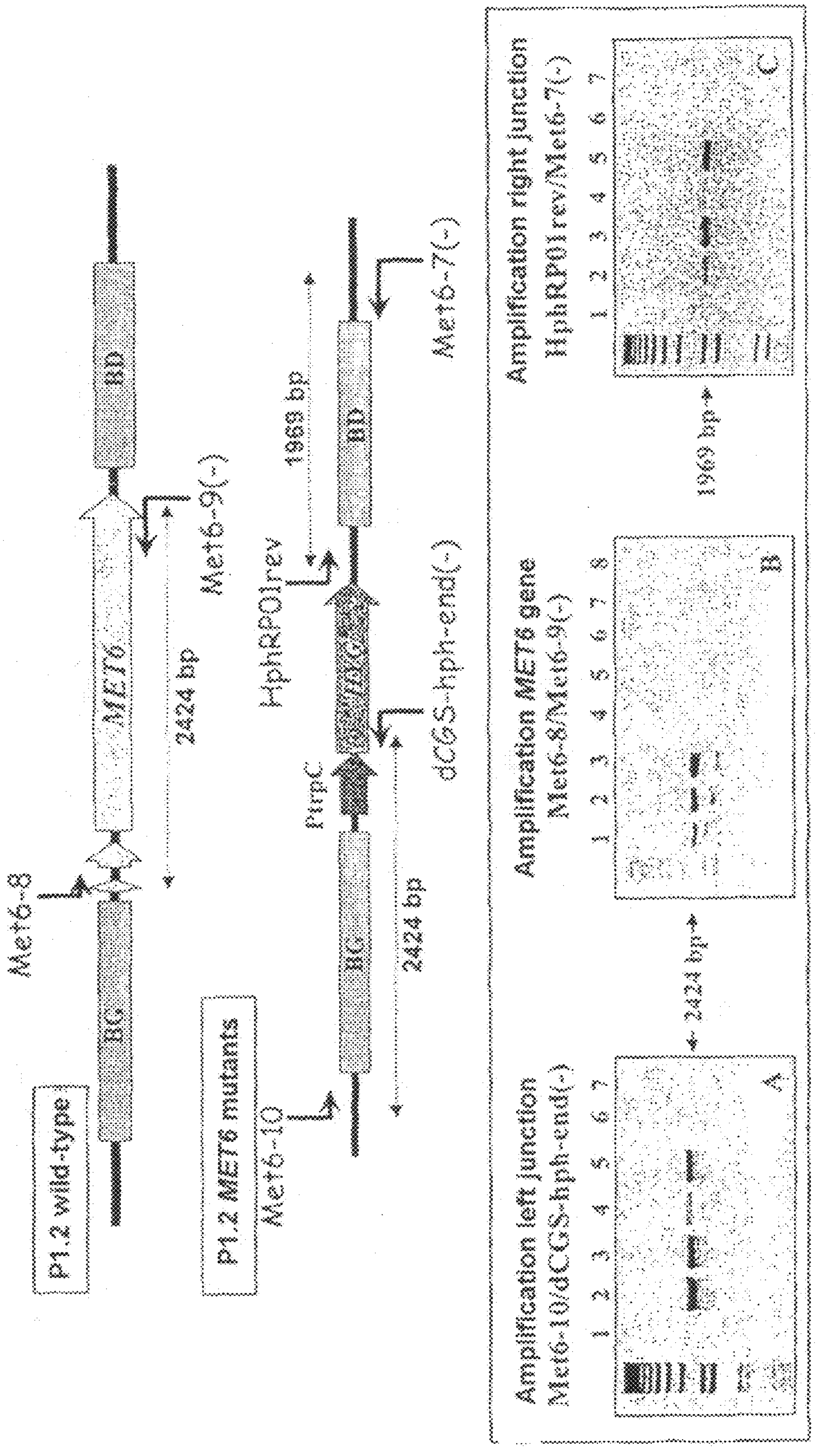
P1.2 wild-type
BG
Met6-8
MET6
2424 bp
Met6-9(-)
BD
P1.2 MET6 mutants
Met6-10
BG
2424 bp
PtrpC
dCGS-hph-end(-)
HphRP01rev
1969 bp
BD
Met6-7(-)
Amplification left junction
Met6-10/dCGS-hph-end(-)
1 2 3 4 5 6 7
A
2424 bp
Amplification MET6 gene
Met6-8/Met6-9(-)
1 2 3 4 5 6 7 8
B
1969 bp
Amplification right junction
HphRP01rev/Met6-7(-)
1 2 3 4 5 6 7
C

USE OF METHIONINE SYNTHASE INHIBITORS FOR THE TREATMENT OF FUNGAL DISEASES OF CROPS

CROSS REFERENCE TO RELATED APPLICATIONS

The present application is a 35 U.S.C. §371 national phase conversion of PCT/EP2005/014209 filed Dec. 20, 2005, which claims priority of French Application No. 04/13628 filed Dec. 21, 2004.

The present invention relates to the use of methionine synthase inhibitors for the treatment of fungal diseases, and more particularly the treatment of fungal diseases of crop plant species.

Fungi are responsible for devastating epidemics which can result in substantial losses of crops of various plant species. The principle of employing inhibitors of enzymes of pathogenic fungi, and of using these enzymes in tests in order to identify new molecules that are active against these fungi, are known per se. However, merely characterizing a fungal enzyme is not sufficient to achieve this objective, the enzyme chosen as a target for potential antifungal molecules must also be essential to the life of the fungus, its inhibition by the antifungal molecule resulting in death of the fungus, or essential to the pathogenesis of the fungus, in which case its inhibition is not lethal for the fungus but merely inhibits its pathogenic capacity. The identification of metabolic pathways and enzymes essential to the pathogenesis and to the survival of the fungus is therefore necessary for the development of novel antifungal products.

The sulfur assimilation pathway comprises incorporation of the sulfate ion ($SO_4^{2-}$), activation thereof, and reduction thereof to reduced sulfur ($S^{2-}$). These steps are catalyzed successively by an ATP sulfurylase (EC 2.7.7.4), an APS kinase (EC 2.7.1.25), a PAPS reductase (EC 1.8.4.8) (APS reductase in photosynthetic organisms, EC 1.8.4.9), and an (NADPH 2) sulfite reductase (EC 1.8.1.2) (a ferredoxin-dependent enzyme in photosynthetic organisms, EC 1.8.7.1). In all autotrophic organisms, the sulfate ion assimilation, activation and reduction pathway is conserved in terms of its general principle; the incorporation of the reduced sulfur into a carbon backbone exhibits considerable variations according to the organisms: bacteria[1] (for example: *Escherichia coli*), plants[2] (for example: *Arabidopsis thaliana*), yeasts (for example: *Saccharomyces cerevisiae*[3]) and filamentous fungi[4]. In fact, in plants and bacteria, the reduced sulfur is incorporated into a molecule at C3 which derives from serine, to form cysteine. The sulfur is then transferred to a molecule at C4 which derives from homoserine, to form homocysteine. This series of reactions forms the direct transsulfuration pathway. Conversely, in *Saccharomyces cerevisiae* (*S. cerevisae*), the sulfur is directly incorporated into a molecule at C4 which derives from homoserine, to form homocysteine (direct sulfhydrylation)[3]. Cysteine is then synthesized from the homocysteine by means of a series of reactions which make up the reverse transsulfuration pathway. In filamentous fungi, the synthesis of homocysteine is carried out both by the direct pathway in plants (direct transsulfuration) and by that of *S. cerevisiae* (direct sulfhydrylation). Furthermore, the synthesis of cysteine is carried out either by means of serine or from homocysteine via the reverse transsulfuration pathway. These various metabolic pathways were defined following the characterization of mutants auxotrophic for cysteine and for methionine in *Neurospora crassa* (*N. crassa*)[5] and *Aspergillus nidulans* (*A. nidulans*)[6]. This model can be extrapolated to all filamentous fungi, including pathogenic fungi of plants (for example, *Magnaporthe grisea, M. grisea*) and of animals (for example, *Aspergillus fumigatus* (*A. fumigatus*)). *M. grisea*, an ascomycete-type pathogen responsible for considerable damage on rice crops, is a model of choice for such an approach. Methionine synthesis in filamentous fungi requires the action of a methionine synthase of vitamin B12-independent type as in plants. The approach described in the study of the methionine synthase gene of *Cryptococcus neoformans*[28], a human pathogen, differs from the present invention. In fact, while animals (including humans) are capable of synthesizing methionine, this step is catalyzed by a vitamin B12-dependent type methionine synthase very different from that of the other eukaryotes such as plants and fungi. The plant methionine synthase exhibits strong homologies at the protein level with that of *M. grisea*, but also exhibits structural-type differences according to the modeling carried out[9,12,27]. Thus, identification of the fungal enzyme and characterization thereof are required in order to determine its specific characteristics, allowing the identification of solely fungal inhibitors. The choice and the application of such inhibitors in methods for treating plant crops will then be specific. Thus, the present invention describes the fact that the mutants of the MET6 gene, and more particular the deletion mutants of the MET6 gene encoding the methionine synthase of *M. grisea* are auxotrophic for methionine and are nonpathogenic. In these mutants, the infectious process is greatly effected at the level of the phase of penetration of the pathogen into the plant cell, but also in terms of its ability to progress in the infected tissues. The pathogenic capacity of the *M. grisea* methionine synthase mutants is partially restored when methionine is added during infection. These results show that the absence of methionine synthase activity is lethal to the fungus during infection. Similar results have been obtained in *Utilago maydis* (*U. maydis*) and *Phytophthora infestans* (*P. infestans*).

BRIEF DESCRIPTION OF THE DRAWING(S)

FIG. 1 is a comparative gene map of wild type Magnaporthe grisea methionine synthase gene and a MET6-deficient mutant thereof.

DESCRIPTION OF THE SEQUENCE LISTING

SEQ ID No. 1: *Magnaporthe grisea* methionine synthase gene
SEQ ID No. 2: *Magnaporthe grisea* methionine synthase cDNA
SEQ ID No. 3: *Magnaporthe grisea* methionine synthase protein sequence
SEQ ID No. 4: Met6-5 primer
SEQ ID No. 5: Met6-6 primer
SEQ ID No. 6: HphRP10 primer
SEQ ID No. 7: Met6-7 primer
SEQ ID No. 8: Met6-10 primer
SEQ ID No. 9: dCGS-hph-end(−) primer
SEQ ID No. 10: Met6-8 primer
SEQ ID No. 11: Met6-9 primer
SEQ ID No. 12: Met6-1 primer
SEQ ID No. 13: Met6-2 primer
SEQ ID No. 14: Met6-3 primer
SEQ ID No. 15: Met6-4 primer
SEQ ID No. 16: *U. maydis* methionine synthase gene
SEQ ID No. 17: *U. maydis* methionine synthase cDNA
SEQ ID No. 18: *U. maydis* methionine synthase protein sequence SEQ ID No. 19: *P. infestans* methionine synthase EST sequence SEQ ID No. 20: deduced *P. infestans* methionine synthase protein sequence.

DESCRIPTION OF THE INVENTION

A subject of the present invention is methods for treating crops against fungal diseases by application of an effective amount of a methionine synthase inhibitor.

In the context of the present invention, the fungal diseases are defined as diseases due to pathogenic plant fungi belonging to the ascomycete, basidiomycete and oomycete families.

A subject of the invention is a method for controlling, in a curative or preventive capacity, phytopathogenic fungi of crops, characterized in that an effective (agronomically effective) and nonphytotoxic amount of a methionine synthase inhibitor is applied to the soil where the plants grow or are liable to grow, to the leaves and/or the fruit of the plants or to the seeds of the plants. The term "effective and nonphytotoxic amount" is intended to mean an amount of inhibitor that is sufficient to allow the control of the developmental cycle or the destruction of the fungi which are present or which may appear on the crops, and that does not result in any notable symptom of phytotoxicity for said crops. Such an amount may vary within broad limits depending on the fungal family to be controlled, the type of crop, the climatic conditions and the compounds included in the antifungal composition according to the invention.

This amount can be determined by systematic field trials, which are within the scope of those skilled in the art.

The methods according to the invention are of use for treating the seeds of cereals (wheat, rye, triticale and barley, in particular), potato, cotton, pea, rapeseed, maize or flax, alternatively the seeds of forest trees or else genetically modified seeds of these plants. The present invention also relates to foliar application to plant crops i.e. to the foliage, the leaves, the fruit and/or the stems of the plants concerned, but also any other type of application. Among the plants targeted by the methods according to the invention, mention may be made of rice, maize, cotton, cereals, such as wheat, barley or triticale, fruit trees, in particular apple trees, pear trees, peach trees, vine, banana trees, orange trees, lemon trees, etc., oil-yielding crops, for example rapeseed or sunflower, market garden and vegetable crops, tomatoes, salads, protein-yielding crops, pea, Solanaceae, for example potato, beetroot, flax, and forest trees, and also genetically modified homologs of these crops.

Among the plants targeted by the method according to the invention, mention may be made of:

- wheat, as regards controlling the following seed diseases: fusaria (*Microdochium nivale* and *Fusarium roseum*), stinking smut (*Tilletia caries, Tilletia controversa* or *Tilletia indica*), *septoria* disease (*Septoria nodorum*); loose smut (*Ustilago tritici*);
- wheat, as regards controlling the following diseases of the parts of the plant above ground: cereal eyespot (*Tapesia yallundae, Tapesia acuiformis*), take-all (*Gaeumannomyces graminis*), foot blight (*F. culmorum, F. graminearum*), head blight (*F. culmorum, F. graminearum, Microdochium nivale*), black speck (*Rhizoctonia cerealis*, powdery mildew (*Erysiphe graminis* form a specie *tritici*), rusts (*Puccinia striiformis* and *Puccinia recondita*) and *septoria* diseases (*Septoria tritici* and *Septoria nodorum*), net blotch (*Drechslera tritici-repentis*);
- barley, as regards controlling the following seed diseases: net blotch (*Pyrenophora graminea, Pyrenophora teres* and *Cochliobolus sativus*), loose smut (*Ustilago nuda*) and fusaria (*Microdochium nivale* and *Fusarium roseum*);
- barley, as regards controlling the following diseases of the parts of the plant above ground: cereal eyespot (*Tapesia yallundae*), net blotch (*Pyrenophora teres* and *Cochliobolus sativus*), powdery mildew (*Erysiphe graminis* form a specie *hordei*), dwarf leaf rust (*Puccinia hordei*) and leaf blotch (*Rhynchosporium secalis*);
- potato, as regards controlling tuber diseases (in particular *Helminthosporium solani, Phoma tuberosa, Rhizoctonia solani, Fusarium solani*), and mildew (*Phytophthora infestans*);
- potato, as regards controlling the following foliage diseases: early blight (*Alternaria solani*), mildew (*Phytophthora infestans*);
- cotton, as regards controlling the following diseases of young plants grown from seeds: damping-off and collar rot (*Rhizoctonia solani, Fusarium oxysporum*), black root rot (*Thielaviopsis basicola*);
- protein-yielding crops, for example pea, as regards controlling the following seed diseases: anthracnose (*Ascochyta pisi, Mycosphaerella pinodes*), fusaria (*Fusarium oxysporum*), gray mold (*Botrytis cinerea*), mildew (*Peronospora pisi*);
- oil-yielding crops, for example rapeseed, as regards controlling the following seed diseases: *Phoma lingam, Alternaria brassicae* and *Sclerotinia sclerotiorum;*
- maize, as regards controlling seed diseases: (*Rhizopus* sp., *Penicillium* sp., *Trichoderma* sp., *Aspergillus* sp. and *Gibberella fujikuroi*);
- flax, as regards controlling seed diseases: *Alternaria linicola;*
- forest trees, as regards controlling damping-off (*Fusarium oxysporum, Rhizoctonia solani*);
- rice, as regards controlling the following diseases of the parts above ground: blast disease (*Magnaporthe grisea*), black speck (*Rhizoctonia solani*);
- vegetable crops, as regards controlling the following diseases of seeds or of young plants grown from seeds: damping-off and collar rot (*Fusarium oxysporum, Fusarium roseum, Rhizoctonia solani, Pythium* sp.);
- vegetable crops, as regards controlling the following diseases of the parts above ground: gray mold (*Botrytis* sp.), powdery mildews (in particular *Erysiphe cichoracearum, Sphaerotheca fuliginea, Leveillula taurica*), fusaria (*Fusarium oxysporum, Fusarium roseum*), leaf spot (*Cladosporium* sp.), *alternaria* leaf spot (*Alternaria* sp.), anthracnose (*Colletotrichum* sp.), *septoria* leaf spot (*Septoria* sp.), black speck (*Rhizoctonia solani*), mildews (for example, *Bremia lactucae, Peronospora* sp., *Pseudoperonospora* sp., *Phytophthora* sp.);
- fruit trees, as regards diseases of the parts above ground: *monilia* disease (*Monilia fructigenae, M. laxa*), scab (*Venturia inaequalis*), powdery mildew (*Podosphaera leucotricha*);
- grapevine, as regards foliage diseases: in particular, gray mold (*Botrytis cinerea*), powdery mildew (*Uncinula necator*), black rot (*Guignardia biwelli*), mildew (*Plasmopara viticola*);
- beetroot, as regards the following diseases of the parts above ground: cercosporia blight (*Cercospora beticola*), powdery mildew (*Erysiphe beticola*), leaf spot (*Ramularia beticola*).

Methionine synthase is a well characterized enzyme that is found in plants and microorganisms (bacteria, yeasts, fungi). The methods of the present invention use methionine synthase inhibitors. In a first embodiment, the invention relates to the use of inhibitors of fungal methionine synthase, more preferably of inhibitors of the methionine synthase of a phytopathogenic fungus, for the treatment of fungal diseases of crops.

Preferably, the methionine synthase is isolated, purified or partially purified from its natural environment. The methionine synthase can be prepared by means of various methods. These methods are in particular purification from natural sources such as cells that naturally express these polypeptides, production of recombinant polypeptides by appropriate host cells and subsequent purification thereof, production by chemical synthesis or, finally, a combination of these various approaches. These various methods of production are well known to those skilled in the art.

In one of the embodiments of the invention, the methionine synthase is purified from an organism that naturally produces this enzyme, for instance bacteria such as *E. coli*, yeasts such as *S. cerevisiae*, or fungi such as *N. crassa* or *M. grisea*.

In a preferred embodiment of the invention, the methionine synthase is overexpressed in a recombinant host organism. The methods of engineering DNA fragments and the expression of polypeptides in host cells are well known to those skilled in the art and have, for example, been described in "Current Protocols in Molecular Biology" Volumes 1 and 2, Ausubel F. M. et al., published by Greene Publishing Associates and Wiley-Interscience (1989) or in Molecular Cloning, T. Maniatis, E. F. Fritsch, J. Sambrook (1982).

In a specific embodiment of the invention, the methionine synthase inhibitors inhibit the methionine synthase of *M. grisea*, of *U. maydis*, and more particularly represented by a sequence comprising the sequence identifier SEQ ID No. 18, or else of *P. infestans*, in particular represented by a sequence comprising the sequence identifier SEQ ID No. 20; said methionine synthase can be encoded by the gene of *M. grisea* represented by a sequence comprising the sequence identifier SEQ ID No. 1, or by the cDNA represented by a sequence comprising the sequence identifier SEQ ID No. 2, by the gene of *U. maydis* represented by a sequence comprising the sequence identifier SEQ ID No. 16, or by the cDNA represented by a sequence comprising the sequence identifier SEQ ID No. 17, or else by the gene of *P. infectans* represented by a sequence comprising the sequence identifier SEQ ID No. 19.

A subject of the present invention is also antifungal compositions comprising a methionine synthase inhibitor and another antifungal compound. Mixtures with other antifungal compounds are particularly advantageous, especially mixtures with acibenzolar-S-methyl, azoxystrobin, benalaxyl, benomyl, blasticidin-S, bromuconazole, captafol, captan, carbendazim, carboxin, carpropamide, chlorothalonil, antifungal compositions based on copper or on copper derivatives such as copper hydroxide or copper oxychloride, cyazofamide, cymoxanil, cyproconazole, cyprodinyl, dichloran, diclocymet, dicloran, diethofencarb, difenoconazole, diflumetorim, dimethomorph, diniconazole, discostrobin, dodemorph, dodine, edifenphos, epoxyconazole, ethaboxam, ethirimol, famoxadone, fenamidone, fenarimol, fenbuconazole, fenhexamid, fenpiclonil, fenpropidine, fenpropimorph, ferimzone, fluazinam, fludioxonil, flumetover, fluquinconazole, flusilazole, flusulfamide, flutolanil, flutriafol, folpet, furalaxyl, furametpyr, guazatine, hexaconazole, hymexazol, imazalil, iprobenphos, iprodione, isoprothiolane, kasugamycin, kresoxim-methyl, mancozeb, maneb, mefenoxam, mepanipyrim, metalaxyl and its enantiomers such as metalaxyl-M, metconazole, metiram-zinc, metominostrobin, oxadixyl, pefurazoate, penconazole, pencycuron, phosphoric acid and its derivatives such as fosetyl-Al, phthalide, picoxystrobin, probenazole, prochloraz, procymidone, propamocarb, propiconazole, pyraclostrobin, pyrimethanil, pyroquilon, quinoxyfen, silthiofam, simeconazole, spiroxamine, tebuconazole, tetraconazole, thiabendazole, thifluzamide, thiophanate, e.g. thiophanate-methyl, thiram, triadimefon, triadimenol, tricyclazole, tridemorph, trifloxystrobin, triticonazole, valinamide derivatives, for instance iprovalicarb, vinclozolin, zineb and zoxamide. The mixtures thus obtained have a broader spectrum of activity. The compositions according to the invention can also comprise one or more insecticides, bactericides, acaricides or pheromones, or other compounds that have a biological activity.

A subject of the present invention is also methods for producing an antifungal composition using a methionine synthase inhibitor.

A subject of the present invention is also methods for preparing antifungal compounds, comprising the identification of compounds which inhibit the enzymatic activity of methionine synthase.

The enzymatic reaction is carried out in the presence of the test compound in order to measure the inhibition of the enzymatic activity of the methionine synthase. All biochemical tests for measuring the enzymatic activity of methionine synthase and therefore identifying compounds which inhibit this enzymatic activity can be used in the methods according to the invention.

A high-throughput biochemical assay is proposed in order to screen for specific inhibitors of this enzyme.

Preferably, the methods for identifying compounds which inhibit the activity of methionine synthase comprise bringing these compounds into contact with methionine synthase in the presence of its substrates: homocysteine, methyl tetrahydrofolate or polyglutamate derivatives of methyl tetrahydrofolate ($(CH_3$—$H_4)PteGlu_n$), and of various cofactors such as phosphate, magnesium and zinc; and measuring the enzymatic activity.

Measuring the enzymatic activity of methionine synthase can be associated with measuring the formation of methionine, of tetrahydrofolate or else of methenyl tetrahydrofolate or of any product thus obtained, or else measuring said activity by any other chemical or enzymatic reaction.

The measurement of the enzymatic activity of methionine synthase can also be carried out in the presence of a coupling enzyme. S-Adenosylmethionine synthase (AdoMetS) can be used as such; it catalyzes the formation of S-adenosylmethionine (S-AdoMet) in the presence of methionine, ATP and magnesium. The measurement of the enzymatic activity of methionine synthase can then be associated with the measurement of the formation of S-adenosylmethionine, of phosphate or of pyrophosphate.

According to another aspect of the invention, the methods for identifying compounds which inhibit the enzymatic activity of methionine synthase comprise expressing methionine synthase in a host organism, purifying the methionine synthase produced by the host organism, bringing these compounds into contact with the purified methionine synthase and its substrates, and measuring the enzymatic activity.

In a preferred embodiment, all these methods comprise an additional step in which it is determined whether said compounds which inhibit the enzymatic activity of methionine synthase inhibit fungal growth and/or pathogenesis.

The present invention therefore relates to methods for identifying compounds which inhibit fungal growth and/or pathogenesis by inhibiting the enzymatic activity of methionine synthase. These methods consist in subjecting a compound, or a mixture of compounds, to an appropriate assay for identifying the compounds which inhibit methionine synthase, and in selecting the compounds which react positively to said assay, where appropriate in isolating them, and then in identifying them.

Preferably, the appropriate assay is an assay of the enzymatic activity of methionine synthase as defined above.

Preferably, a compound identified according to these methods is subsequently tested for these antifungal properties according to methods known to those skilled in the art. Preferably, the compound is evaluated by means of phenotypic tests such as pathogenesis assays on detached leaves or on whole plants.

The term "compound" is intended to mean, according to the invention, any chemical compound or mixture of chemical compounds, including peptides and proteins.

The term "mixture of compounds" is understood to mean, according to the invention, at least two different compounds, such as, for example, the (dia)stereoisomers of a molecule, mixtures of natural origin derived from the extraction of biological material (plants, plant tissues, bacterial cultures, cultures of yeasts or of fungi, insects, animal tissues, etc.) or reaction mixtures that have not been purified or have been completely or partially purified, alternatively mixtures of products derived from combinatorial chemistry techniques.

Finally, the present invention relates to novel fungal pathogenesis-inhibiting compounds which inhibit the enzymatic activity of methionine synthase, in particular the compounds identified by means of the methods according to the invention and/or the compounds derived from the compounds identified by means of the methods according to the invention.

Preferably, the fungal pathogenesis-inhibiting compounds which inhibit the enzymatic activity of methionine synthase are not general inhibitors of enzymes. Also preferably, the compounds according to the invention are not compounds already known to have an antifungal activity and/or an activity on fungal pathogenesis.

EXAMPLE 1

Characterization of the Methionine Synthase Gene in Fungi

The methionine synthase gene was identified in the genome of *M. grisea* version V2 using the protein sequence of the methionine synthase of *A. nidulans*[7] (NCBI, accession number: AAF82115) as model. The complete nucleotide sequence of the methionine synthase gene located on Contig 2.150 (MG_contig_2.150, position 6196-8629, complementary strand, SEQ ID No. 1) comprises 3 exons corresponding to a cDNA of 2301 bp (SEQ ID No. 2) which encodes a polypeptide of 766 amino acids (SEQ ID No. 3). The sequence of the g ene and the splicing resulting in the definitive messenger could be confirmed by virtue of the numerous ESTs identified in the various public and private bases. The *M. grisea* methionine synthase is encoded by a single gene as in *A. nidulans*[7]. Analysis of the primary protein sequence deduced from the putative cDNA shows from 48% to 79% homology with the vitamin $B_{12}$-independent methionine synthases of *S. cerevisae* (P05694), of *A. nidulans* (AAF82115), of the bacterium *E. coli* (P13009) and of the plant *A. thaliana* (AAF00639).

The primary sequence of the *M. grisea* methionine synthase has two conserved domains corresponding to the methionine synthase domain (334 residues, $E=4e^{-116}$, pfam01717) characteristic of this enzyme. This domain allows the production of methionine by transfer of a methyl group from methyl tetrahydrofolate triglutamate to homocysteine. This region is located in the C-terminal part of the protein. A second domain, COG0620 or methionine synthase II (methyltransferase) concerns the N-terminal part of the protein (330 amino acids)[8]. It has recently been possible to determine the specificity of each of these domains with respect to the substrates of the enzyme, homocysteine and methyl tetrahydrofolate, and to the reaction product, methionine, on the enzyme crystallized from *A. thaliana*[9].

The primary sequence of the *M. grisea* methionine synthase was used to search for orthologs in the various fungal species whose genome is partially or completely sequenced. These various primary sequences were subsequently compared with the methionine synthases described in various organisms such as plants, bacteria and animals. The characterization of the structure of the genes (introns+exons) and of the primary amino acid sequences was carried out using the appropriate programs (tblastn; FGENSH; PSI-PHI-BLAST). According to this procedure, methionine synthase could be characterized in several fungi (ascomycetes and basidiomycetes) and a phytopathogenic oomycete (*P. sojae* and *P. infestans*). A phylogenetic tree for methionine synthase could be established and the representation obtained shows that the *M. grisea* methionine synthase belongs to the methionine synthases of ascomycetes and that it is distant from those of basidiomycetes. Overall, the tree obtained is in agreement with that which retraces the phylogenetic origin of these organisms[10].

EXAMPLE 2

Deletion of the *Magnaporthe grisea* Methionine Synthase Gene

The study of the role of the methionine synthase gene in the development and the infectious process of *M. grisea* was carried out by studying the phenotype of deletion mutants of this gene. The strategy for obtaining deletion mutants is based on replacing the MET6 gene with a mutant allele in which the MET6 open reading frame has been replaced with a cassette for resistance to an antibiotic for selection of the transformants (hygromycin).

The construction of this vector for replacing the *M. grisea* MET6 gene is carried out in two steps: (i) PCR amplification of the regions which border this gene and which correspond respectively to genomic regions of approximately 1 kb located on either side of MET6, (ii) ligation of these genomic DNA fragments to a gene for resistance to an antibiotic that makes it possible to select the transformants. Thus, the PCR fragments used to replace the gene consist of the two regions which are referred to as left border and right border of the gene studied (FIG. 1). We selected the hygromycin resistance gene (HYG, comprising the PtrpC promoter, the coding portion of the hygromycin resistance gene hph) as selectable gene. Ligation of the HYG gene is first carried out via the SacII/BglII sites and the EcoRI/SacII sites of the left border (Met6-1/Met6-2 primers) of the MET6 gene. The right border of the MET6 gene (Met6-3/Met6-4 primers) is then introduced via the PmeI site downstream of the hph gene (FIG. 1). The replacement vector therefore comprises the left border (BG) of the MET6 gene (promoter region of 1475 bp), the HYG cassette (1400 bp) and the right border (BD) of the MET6 gene (terminator region of 1251 bp). The ligation product (BG-hph-BD) was subsequently cloned into a plasmid vector. The MET6 gene replacement cassette was subsequently amplified from the corresponding plasmid by PCR with primers specific for the ends of the borders of the MET6 gene (Met6-5/Met6-6 primers). Sequencing of the junctions between the borders and the HYG cassette of the replacement vector made it possible to verify the construction. The PCR product (1 μg), purified by agarose gel electrophoresis, is then used to transform protoplasts of the *M. grisea* P1.2 wild-type strain according to conventional techniques developed in the laboratory. The products derived from the transformation are selected on a medium containing the corresponding antibiotic (hygromycin).

EXAMPLE 3

Identification and Trophic Characterization of the met6Δ::hph Deletion Mutants Obtained by Gene Replacement The primary transformants are selected for their ability to develop in the presence of hygromycin. The identification of the met6Δ::hph mutants is carried out by measuring the differential growth of the transformants on a minimum medium containing hygromycin, supplemented or not supplemented with 1 mM methionine. The met6Δ::hph mutants are incapable of developing on this minimum medium, but they have a normal growth on this minimum medium supplemented with methionine. The frequency of the mutants is of the order of 20% of the primary transformants analyzed under our experimental conditions. These mutants were subsequently genetically purified by isolation of monosphores.

The five met6Δ::hph mutants obtained (4.1, 15.1, 22.1 and 23.1) are incapable of developing on a minimum medium that allows growth of the P1.2 wild-type strain. The addition of methionine to the minimum medium restores growth of the mutants. The trophic complementation of the met6Δ::hph mutants by the addition of methionine indicates that the methionine synthase is affected by the MET6 gene deletion.

The addition of sulfur donors such as cysteine or glutathione (precursors of homocysteine, a substrate from methionine synthase) is not sufficient to restore the growth of the *M. grisea* met6 Δ::hph mutants. Consequently, there is not parallel pathway which would use methyl tetrahydrofolate or its polyglutamate derivatives for the synthesis of methionine in this fungus. Thus, the de novo synthesis of methionine is catalyzed solely by methionine synthase. The activity of this enzyme is therefore essential to the development of the fungus.

On the other hand, in the presence of S-adenosylmethionine (SAM or AdoMet), a compound which derives directly from methionine and which is essential to the cell cycle, or of S-methylmethionine (SMM), a compound which is synthesized in plants, the *M. grisea* met6Δ::hph mutants are capable of developing, although with a reduced growth compared to the P1.2 wild-type strain. SAM and SMM are capable of penetrating and of being metabolized to methionine by *M. grisea*. This mechanism is probably similar to that described in the yeast *S. cerevisae*. In fact, in this ascomycete fungus, SAM and SMM are incorporated into the cell via the transporters SAM3 and MPP1, and are subsequently converted to methionine in the presence of homocysteine by homocysteine-5-methyltransferases (SAM4 and MHT1) which use SAM or SMM, respectively, as methyl group donor (*S. cerevisae*)[11]. According to our experimental conditions, the addition of SAM (1 mM) to the minimum medium is more effective than that of SMM in restoring the growth of the met6Δ::hph mutants. These results suggest that *M. grisea* has transporters and homocysteine methyltransferases similar to those described in *S. cerevisae*. An analysis of the *M. grisea* genome by sequence homology search (tBlastN) with respect to the yeast SAM4 and MHT1 proteins makes it possible to demonstrate a gene which is an ortholog of SAM4 in *M. grisea*. It would appear that filamentous fungi have only one gene (no ortholog of MHT1). According to our results (better growth on SAM than on SMM), this protein could have a greater affinity for SAM than for SMM.

Several "ectopic" transformants, corresponding to transformants which have integrated the replacement vector BG-hph-BD at a locus other than that of the MET6 gene, were also analyzed. These hygromycin-resistant ectopic transformants are capable of developing on a minimum medium. The methionine synthase gene is therefore functional in these ectopic transformants and the vector has been inserted at a locus of the genome which has no effect on the development of the pathogen under our experimental conditions (ability to develop on the minimum or complete medium, sporulation).

EXAMPLE 4

Molecular Characterization of the met6Δ::hph Mutants

The met6Δ::hph mutants are cultured in a medium containing methionine (1 mM) in order to extract the genomic DNA, which will be used to perform a molecular analysis of the MET6 locus by PCR and by Southern hybridization.

The molecular analysis of the transformants is carried out by amplification of the genomic regions of the MET6 locus using the various specific primers for replacing the wild-type allele of the MET6 gene of P1.2 with the mutant allele met6Δ::hph. These PCRs are carried out for each mutant with specific oligonucleotides. The reactions use oligonucleotides which hybridize: firstly, with the hygromycin resistance gene hph and, secondly, with a genomic sequence of the MET6 locus located outside the MET6 region used to construct the replacement vector (left junction and right junction); with the sequences homologous to the MET6 gene. Thus, the amplification of a fragment of 1969 bp (left junction) or of 2447 bp (right junction) occurs only in the case of replacement of the wild-type gene with the met6Δ::hph gene of the construct (primers HphRP01rev (SEQ ID No. 6)/Met6-7(−) (SEQ ID No. 7) and Met6-10 (SEQ ID No. 8)/dCGS-hph-end(−) (SEQ ID No. 9) (FIG. 1)). No amplification is obtained in the case of the P1.2 wild-type strain or of the ectopic transformants. Similarly, the absence of amplification of the MET6 gene in the met6Δ::hph mutants (primers Met6-8, SEQ ID No. 10/Met6-9, SEQ ID No. 11) (FIG. 1) is an indication that the MET6 gene is indeed absent in these transformants. On the other hand, with these primers, a fragment of 2424 bp is amplified in the P1.2 wild-type strain and in the ectopic transformants. Only the PCRs carried out with the mutants 22.2 and 23.1 give the expected results with these three types of PCR. No amplification could be obtained, for unexplained reasons, with the mutants 4.1 and 15.1 in the PCRs Met6-10 (SEQ ID No. 8)/dCGS-hph-end (SEQ ID No. 9) and hphRP01 (SEQ ID No. 6)/Met6-7(−), SEQ ID No. 7).

An analysis by Southern hybridization after digestion of the genomic DNA with the BamH1 restriction enzyme was carried out and the hybridization signals obtained for the 4 mutants were compared with those obtained with the P1.2 wild-type strain and the ectopic transformant (19.1). Using the (Met6-1 (SEQ ID No. 12)/Met6-2 (SEQ ID No. 13)) PCR fragment corresponding to the MET6 left border present in the replacement vector (MET6 promoter region) as probe, 2 bands are observed for the mutants, the sizes of which are different from those of the P1.2 wild-type strain and of the ectopic transformant (19.1). The signal corresponds to the MET6 promoter region in the P1.2 wild-type strain and the ectopic transformant 19.1. The latter also shows a hybridization signal corresponding to the replacement vector inserted into another genomic region. A similar result is obtained using a (Met6-3 (SEQ ID No. 14)/Met6-4 (SEQ ID No. 15)) PCR fragment corresponding to the MET6 right border present in the replacement vector (MET6 terminator region). With a probe specific for the inserted gene (hph), only the met6Δ::hph mutants and the ectopic transformant 19.1 show a hybridization signal corresponding either to the presence of hph at the MET6 locus (mutants) or to the replacement vector BG-met6Δ::hph-BD (ectopic). The latter results indicate that the various mutants analyzed are identical at the molecular level and contain just one copy of the hph gene inserted as the MET6 locus in place of the MET6 coding phase.

EXAMPLE 5

Analysis of the Pathogenic Capacity of the *Magnaporthe grisea* met6Δ::hph Mutants The pathogenic capacity of the *M. grisea* met6 Δ::hph mutants was evaluated by means of an infection test on barley leaves under survival conditions and on whole barley and rice plants. This analysis was followed by measurement of the spore germination rate, of appressorial differentiation and of penetration into barley leaves. The spores of the P1.2 wild-type strain and of the met6Δ::hph mutants 4.1, 15.1, 22.1, 23.1 and 24.1 are harvested after growth for 14 days on a rice flour-based medium containing 1 mM. The plant material used is barley (cv. Express) and rice (cv. Sariceltik).

In the experiments carried out on barley leaves under survival conditions, the leaves are incubated on an agar medium (1% agar-$H_2O$) containing kinetin (2 mg·ml$^{-1}$) in a temperate climatic chamber (26° C.) at high humidity (100%) and under light of 100 microeinsteins. During infection, the spores are deposited onto the leaves either in the form of droplets (35 µl) or by coating the surface of the leaves with the suspension of spores using a cotton wool bud. These experiments are carried out in the absence or in the presence of 1 mM methionine throughout the incubation or for only 24 hours. The spore concentration is $3\times10^4$ spores/ml to $1\times10^5$ spores/ml in water. The appearance of the symptoms caused by *M. grisea* is then observed for at least 7 days of incubation. Inoculation of barley leaves under survival conditions, with spores of the *M. grisea* wild-type strain P1.2, causes necroses characteristic of the development of the fungus in the infected leaf (sporulating lesions). Conversely, the met6Δ::hph mutants 4.1, 15.1, 22.1, 23.1 and 24.1 do not cause any symptom on the barley leaves, regardless of the method of inoculation, and are therefore nonpathogenic. The addition of methionine to the met6Δ::hph mutant spores makes it possible to partially restore their pathogenic capacity (development of characteristic but nonsporulating lesions). Furthermore, under our experimental conditions, we did not observe any marked differences between the infections carried out with injured or noninjured leaves. These observations suggest that the met6Δ::hph mutants are incapable of penetrating barley leaves, even injured barley leaves. The yellowing of the leaves observed in the experiments carried out with spreading of the spores by coating is probably due to premature ageing of the leaves under our experimental conditions. The results are summarized in the following table:

TABLE I

Estimation of the pathogenic capacity of the *Magnaporthe grisea* met6Δ::hph mutants with respect to barley

| | Barley leaves under survival conditions - *Magnaporthe grisea* 3 x 10$^4$ spores/ml | |
|---|---|---|
| | Without methionine | With 1 mM methionine |
| Wild-type strains | | |
| P1.2 | +++ | +++ |
| Ectopic mutant strains | | |
| Ectopic 19.1 | +++ | +++ |
| Ectopic 20.1 | +++ | +++ |
| met6Δ::hph mutants | | |
| 4.1 | 0 | + |
| 15.1 | 0 | + |
| 22.1 | 0 | + |
| 23.1 | 0 | + |

Legend: 0: no lesions; +: nonsporulating necroses (lesions); +++: sporulating lesions The observation and the quantification of the various steps of the infection (germination, formation of the appressorium and penetration) are carried out based on an inoculation of barley leaves under survival conditions with drops of 35 µl of a suspension of spores ($3\times10^5$ spores/ml). After 24 hours, the epidermis of the leaf is peeled in order to observe, under the microscope, the number of germinated spores that have differentiated an appressorium and the number of events of penetration into the epidermal cell. A solution of calcofluor at 0.01% makes it possible to cause an intense fluorescence of the walls of the fungal cells located at the surface of the plant (the hyphae located in the epidermal cell are not colored). These observations (Table II) demonstrate that the met6Δ::hph mutants have a slightly reduced germination (−10% to −40% compared to the wild-type strain). Their appressorial differentiation rate is also slightly reduced (0% to −30% compared to the wild-type strain). On the other hand, these mutant appressoria are incapable of penetrating into the foliar tissues.

TABLE II

Development of the *Magnaporthe grisea* met6Δ::hph mutants on barley

| *M. grisea* strains | % germination | % appressorium/ germinated spores | % penetration |
|---|---|---|---|
| ΔMET6-4.1 | 45 | 52 | 0 |
| ΔMET6-15.1 | 70 | 66 | ND |
| ΔMET6-22.1 | 62 | 80 | ND |
| ΔMET6-23.1 | 37 | 63 | 0 |
| Wild-type P1.2 | 80 | 80 | 100 |
| Ectopic 19.1 | 80 | 80 | 100 |
| Ectopic 20.1 | 80 | 80 | ND |

ND: not determined

The formation of appressoria is also observed under an artificial condition where the spores are germinated on teflon membranes with or without the addition of methionine (1 mM concentration under our experimental conditions). These very hydrophobic membranes mimic the surface of the leaf, thereby making it possible to induce the formation of appressoria and to readily measure the appressorial differentiation rate.

In conclusion, the *M. grisea* met6Δ::hph mutants are therefore incapable of penetrating into the plant, although they differentiate appressoria. These results show that these mutants have nonfunctional appressoria.

Pots containing 3-week-old barley plants (corresponding to the emergence of the second leaf) are subjected to spraying with a suspension of *M. grisea* spores (10 ml of water containing spores at the concentration of $3\times10^4$ spores/ml and 0.3% gelatin for adhesion of the water droplets to the leaves). The observations of the symptoms are carried out for at least 8 days after spraying. The barley plants treated with the wild-type strain (P1.2) and the ectopic transformants (19.1 and 20.1) show necrotic lesions caused by the development of the fungus in the infected leaves. On the other hand, no symptom of disease was observed in the case of the inoculation with the *M. grisea* met6Δ::hph mutants. These mutants are therefore considered to be nonpathogenic. Furthermore, this study indicates, like the analysis carried out with the barley leaves under survival conditions, that the amount of methionine (or of other compounds that derive from methionine, such as SAM and SMM) in the tissues of the leaf is insufficient to complement the deficiency in methionine synthesis of the met6Δ::hph mutants. Thus, the pathway demonstrated in the in vitro experiments (complementation in the presence of SAM and of SMM) does not appear to be functional in the fungus while it is growing in the plant.

The met6Δ::hph mutants obtained correspond to the deletion of the coding phase of the MET6 gene which is replaced by the hph gene, conferring hygromycin resistance. These mutants are incapable of synthesizing methionine from homocysteine and are therefore incapable of multiplying on a minimum medium. The addition of methionine to this minimum medium is essential for the development of these mutants. The met6Δ::hph mutants do not cause any symptom of disease when they are used to inoculate barley leaves either under survival conditions, or whole plants, even at high spore concentrations. Thus, methionine synthesis by methionine synthase is essential to the development of the fungus, both in vitro and in planta.

The met6Δ::hph mutants can differentiate an appressorium in the absence of methionine. This aspect indicates that the spore can possess a not insignificant store of methionine allowing synthesis of proteins and metabolites necessary for the development of this cell. This store must come from the methionine that was supplied to the mutant in order to allow its growth and its sporulation on the rice flour-based medium used (containing 1 mM of methionine). On the other hand, the absence of penetration of the met6Δ::hph mutants into the leaves indicates that said mutants differentiate nonfunctional appressoria incapable of directing penetration of the fungus into the plant. It is probable that the mutant appressoria have rapidly exhausted their methionine stores. In fact, the addition of methionine to the mutant spores allows penetration into the plant and the beginning of development in the leaf. However, said development is not complete and the absence of formation of sporulating lesions suggests that, once the methionine store supplied to the spores is exhausted, the plant is incapable of covering the methionine needs of the mutants.

EXAMPLE 6

Methods for Assaying and Characterizing Molecules which Inhibit the Enzymatic Activity of Methionine Synthase The method involves the characterization of all molecules whose action inhibits the consumption of substrates or the formation of products determined according to direct or indirect techniques (which include the use of a “coupling” enzyme for measuring the activity of methionine synthase). Methionine synthase catalyzes an irreversible reaction in the presence of homocysteine, of methyl tetrahydrofolate (n=1) or of its polyglutamate derivatives ($n\geqq3$) in the presence of various cofactors (phosphate, magnesium, zinc) according to known assays described in the literature[12,13,14,15,27]. The methodology includes determining methionine or the folate derivatives produced, by techniques for separating compounds by reverse phase HPLC chromatography[16]. The assaying of the tetrahydrofolate produced during the reaction after it has been converted to methenyl tetrahydrofolate can be carried out on a spectrophotometer at 350 nm, since the methyl tetrahydrofolate substrate is not detectable under the experimental conditions described in the procedure[17]. A proposed alternative is to assay the methionine synthase activity in the presence of S-adenosylmethionine synthetase. In this assay, the S-adenosylmethionine synthetase (AdoMetS) of *M. grisea* will preferably be used, but any of the AdoMetS can be used as a “coupling” enzyme. The AdoMetS enzyme catalyzes the irreversible reaction which, in the presence of methionine, ATP and magnesium, produces S-adenosylmethionine (SAM), phosphate and pyrophosphate.

The methionine synthase activity is assayed, in the end, through the amount of SAM, of phosphate or of pyrophosphate produced, by means of a colorimetric method and/or on a spectrophotometer after conversion of the products in the presence of a coupling enzyme or by means of any other chemical or enzymatic reaction for measuring methionine synthase activity. These various methodologies are the subject of many descriptions in the literature and can be adapted according to the experimenter[18,19,20,21,22,23]. For example, the sensitivity of the method for assaying methionine synthase activity in the presence of SAM synthetase can be improved through the addition of a pyrophosphatase which converts the pyrophosphate into 2 mol of phosphate. Thus, for each mole of methionine synthesized, the method produces 3 mol of phosphate.

Purification of *Magnaporthe grisea* Methionine Synthase

The production of a large amount of methionine synthase is carried out using techniques that use expression vectors for overproduction of the protein in bacteria or yeast. The technique preferably uses cloning of the cDNA into an expression vector which makes it possible to integrate a His-Tag extension at the N-terminal or C-terminal end of the protein. For example, when the pET-28b(+) vector (Novagen)[24] is selected, the 2301 bp cDNA is cloned into NdEI and EcoRI according to conventional molecular biology techniques. The construct obtained, called pET-28-MgMET6, is introduced into the *Escherichia coli* BL21 type DE3 (pLysS) bacterial strain and the expression is produced after induction with IPTG (0.5 mM). The recombinant bacteria are cultured at 28° C. for 4 hours. The cells are then harvested by centrifugation and the pellet obtained is resuspended in lysis buffer suitable for the stability of the protein. After sonication of the preparation, the soluble fraction containing the recombinant protein, obtained after centrifugation, is loaded onto a column of Ni-NTA agarose type. The purification and the elution of the enzyme are then carried out after several successive washes of the matrix with an imidazole solution. The procedure follows the protocol define by Qiagen[25].

After elution, the protein fraction containing the recombinant methionine synthase is concentrated by ultrafiltration and subjected to molecular filtration on PD10 (Pharmacia)[27] in order to remove all traces of imidazole. The purification of the recombinant protein can be accompanied by a second step consisting of molecular filtration by chromatography on Superdex S200 (Pharmacia)[26] or of ion exchange chromatography on MonoQ HR10/10 (Pharmacia)[26]. The activity of the methionine synthase is followed during the purification, using the appropriate direct measurement assay.

BIBLIOGRAPHY

[1] Saint-Girons I, Parsot C, Zakin M M, Barzu O and Cohen G N (1988) Methionine biosynthesis in enterobacteria: biochemical regulataory, and evolutionary aspects. Crit. Rev. Biochem. 23, S1-S42

[2] Droux M (2004) Sulfur assimilation and the role of sulfur in plant metabolism: a survey. Photosyn. Res. 79, 331-348

[3] Thomas D and Surdin-Kerjan Y (1997) Metabolism of sulfur amino acids in *Saccharomyces cerevisae*. Microbiol. Mol. Biol. Rev. 61, 503-532

[4] Marzluf G A (1997) Molecular genetics of sulfur assimilation in filamentous fungi and yeast. Annu. Rev. Microbiol. 51, 73-96

[5] Perkins D D, Radford A, Newmeyer D and Björkman M (1982) Chromosomal loci of *Neurospora crassa*. Microbiol. Rev. 46, 426-570

[6] Paszewski A and Grabski J (1974) Regulation of S-amino acids biosynthesis in *Aspergillus nidulans*. Mol. Gen. Genet. 132, 307-320

[7] Grynberg M, Piotrowska M, Pizzinini E, Turner G and Paszewski A (2001) The *Aspergillus nidulans* metE gene is regulated by a second system independent from sulphur metabolite repression. Biochem. Biophys. Acta 1519, 78-84

[8] Marchler-Bauer A, Anderson J B, DeWeese-Scott C, Fedorova N D, Geer L Y, He S, Hurwitz D I, Jackson J D, Jacobs A R, Lanczycki C J, Liebert C A, Liu C, Madej T, Marchler G H, Mazumder R, Nikolskaya A N, Panchenko A R, Rao B S, Shoemaker B A, Simonyan V, Song J S, Thiessen P A, Vasudevan S, Wang Y, Yamashita R A, Yin J J and Bryant S H (2003) CDD: a curated Entrez database of conserved domain alignments. Nucleic Acids Res. 31, 383-387.

[9] Ferrer J L, Ravanel S, Robert M and Dumas R (2004) Crystal structures of cobalamin-independent methionine synthase complexed with Zn, homocysteine and methyltetrahydrofolate. J. Biol. Chem., in press.

[10] Latijnhouwers M, de Wit P J and Govers F (2003) Oomycetes and fungi: similar weaponry to attack plants. Trends Microbiol. 11, 462-469

[11] Thomas D, Becker A and Surdin-Kerjan Y (2000) Reverse methionine biosyntheses from S-adenosylmethionine in Eukaryotic cells. J. Biol. Chem. 275, 40718-40724

[12] Eichel J, Gonzalez J C, Hotze M, Matthews R G and Schroder J (1995) Vitamin $B_{12}$-independent L-methionine synthase from a higher plant (*Cataranthus roseus*): molecular characterization, regulation, heterologous expression, and enzyme properties. Eur. J. Biochem. 230, 1053-1058

[13] Eckermann C, Eichel J and Schroder J (2000) Plant methionine synthase: new insights into properties and expression. Biol. Chem. 381, 695-703

[14] Gonzalez J C, Peariso K, Penner-Hahn J E and Matthews R G (1996) Cobalamin-independent methionine synthase from *Escherichia coli*: involvement: a zinc mettalloenzyme. Biochemistry 35, 12228-12234

[15] Whifield C D, Steers E J Jr and Weissbach H (1970) Purification and properties of 5-methyltetra-hydropteroyltriglutamate-homocysteine transmethylase. J. Biol. Chem. 245, 390-401.

[16] Huang L, Zhang J, Hayakawa T and Tsuge H (2001) Assays of methylenetetrahydrofolate reductase and methionine synthase activities by monitoring 5-methyl-tetrahydrofolate and tetrahydrofolate using High-Performance Liquid Chromatography Liquid Chromatography with fluorescence detection. Anal. Biochem. 299, 253-259

[17] Drummond J T, Jarrett J, Gonzalez J C, Huang S and Matthews R G (1995) Characterization of nonradioactive assays for cobalamin-dependent and cobalamin-independent methionine synthase enzymes. Anal. Biochem. 228, 323-329

[18] Lanzetta P A, Alvarez L J, Reinach P S and Candia O A (1979) An improved assay for nanomole amounts of inorganic phosphate. Anal. Biochem. 100, 95-97

[19] Rosalyn H U, Haugland R P, Malekzadeh M N and Haugland R P (1996) A spectrophotometric method to measure enzymatic activity in reactions that generate inorganic pyrophosphate. Anal. Biochem. 243, 41-45

[20] Cannon L M, Butler F N, Wan W and Zhou Z S (2002) A stereospecific colorimetric assay for (S,S)-adenosyl-methionine quantification based on thiopurine methyltransferase-catalyzed thiol methylation. Anal. Biochem. 308, 358-363

[21] Katewa S D and Katyare S S (2003) A simplified method for inorganic phosphate determination and its application for phosphate analysis in enzyme assays. Anal. Biochem. 323, 180-187

[22] Vazquez M J, Rodriguez B, Zapatero C and Tew D G (2003) Determination of phosphate in nanomolar range by an enzyme-coupling fluorescent method. Anal. Biochem. 320, 292-298

[23] Gawronski J D and Benson D R (2004) Microtiter assay for glutamine synthetase biosynthetic activity using inorganic phosphate detection. Anal. Biochem. 327, 114-118

[24] Novagen: http://www.merckbiosciences.co.uk/g.asp?f=NVG/home.html

[25] Qiagen: http://www1.qiagen.com

[26] Pharmacia: https://chromatography.amershambiosciences.com

[27] Ravanel S., Block M A., Rippert P., Jabrin S., Curien G., Rébeillë F and Douce R (2004) Methionine metabolism in plants: chloroplasts are autonomous for de novo methionine synthesis and can import S-adenosylmethionine from the cytosol. J. Biol. Chem. 279, 22548-22557.

[28] Pascon R. C., Ganous T. M., Kingbury J. M., Cox G. M. and McCusker J. H. (2004) *Cryptococcus neoformans* methionine synthase: expression analysis and requirement for vehicle.

What is claimed is:

1. A method for identifying a compound that is an inhibitor of methionine synthase comprising:

(A) bringing said compound into contact with methionine synthase in the presence of homocysteine and of methyl tetraglutamate or its polyglutamate derivatives, and of cofactors and measuring the reduction in the formation of methionine as compared to a control carried out in the absence of said compound; or (B) bringing said compound into contact with methionine synthase in the presence of homocysteine and of methyl tetraglutamate or its polyglutamate derivatives, of S-adenosylmethionine synthetase, of ATP and of Mg, and of cofactors, and measuring the reduction in the formation of S-adenosylmethionine, phosphate or pyrophosphate as compared to a control carried out in the absence of said compound;

wherein the methionine synthase is selected from the group consisting of:

(1) the methionine synthase that is derived from *Magnaporthe grisea* and comprises SEQ ID No. 3, and is encoded by a sequence comprising SEQ ID No. 1 or SEQ ID No. 2;

(2) the methionine synthase that is derived from *Ustilago maydis* and comprises SEQ ID No. 18, and is encoded by a sequence comprising SEQ ID No. 16 or SEQ ID No. 17; and (3) the methionine synthase that is derived from *Phytophora infestans* and comprises SEQ ID No. 20, and is encoded by a sequence comprising SEQ ID No. 19; and (C) identifying the compound that reduces enzymatic activity and/or reduces the formation of methionine as an inhibitor of methionine.

2. The method of claim 1 wherein the methionine synthase is derived from *Magnaporthe grisea.*

3. The method of claim 1 wherein the methionine synthase is derived from *Ustilago maydis.*

4. The method of claim 1 wherein the methionine synthase is derived from *Phytophthora infestans.*

5. The method of claim 1 wherein the identification of compounds that inhibit the enzymatic activity of methionine synthase comprises the steps of:

bringing said compound into contact with methionine synthase in the presence of homocysteine and of methyltetraglutamate or its polyglutamate derivatives, and of cofactors; and measuring the reduction in the formation of methionine as compared to a control carried out in the absence of said compound.

6. The method of claim 5 wherein the identification of compounds that inhibit the enzymatic activity of methionine synthase comprises the steps of:

bringing said compound into contact with methionine synthase in the presence of homocysteine, of methyl tetrahydrofolate and of phosphate, magnesium and zinc; and measuring the reduction in the formation of methionine as compared to a control carried out in the absence of said compound.

7. The method of claim 1 wherein the identification of compounds that inhibit the enzymatic activity of methionine synthase comprises the steps of:

bringing said compound into contact with methionine synthase in the presence of homocysteine, of methyl tetrahydrofolate or its polyglutamate derivatives, of S-adenosylmethionine synthetase, of ATP and of Mg, and of cofactors; and measuring the reduction in the formation of S-adenosylmethionine, phosphate or pyrophosphate as compared to a control carried out in the absence of said compound.

8. The method of claim 7 wherein the identification of compounds that inhibit the enzymatic activity of methionine synthase comprises the steps of:

bringing said compound into contact with methionine synthase in the presence of homocysteine, of methyl tetrahydrofolate or its polyglutamate derivatives, of S-adenosylmethionine synthetase, of ATP and of Mg, and of cofactors; and measuring the reduction in the formation of phosphate as compared to a control carried out in the absence of said compound.

9. The method of claim 1 wherein the identification of compounds that inhibit the enzymatic activity of methionine synthase comprises the steps of:

expressing methionine synthase in a host organism;

purifying the methionine synthase produced by said host organism;

bringing said compound into contact with said purified methionine synthase in the presence of homocysteine, of methyl tetrahydrofolate, and of phosphate, magnesium and zinc; and measuring the reduction in the formation of methionine as compared to a control carried out in the absence of said compound.

10. The method of claim 1 wherein the identification of compounds that inhibit the enzymatic activity of methionine synthase comprises the steps of:

expressing methionine synthase in a host organism;

purifying the methionine synthase produced by said host organism;

bringing said compound into contact with said purified methionine synthase in the presence of homocysteine, of methyl tetrahydrofolate or its polyglutamate derivatives, of S-adenosylmethionine synthetase, of ATP and of Mg, and of cofactors; and measuring the reduction in the formation of S-adenosylmethionine, phosphate, or of pyrophosphate as compared to a control carried out in the absence of said compound.

11. A method for identifying a compound that is an inhibitor of methionine synthase comprising:

(A) bringing said compound into contact with methionine synthase in the presence of homocysteine and of methyl tetraglutamate or its polyglutamate derivatives, and of cofactors and measuring the reduction in the formation of methionine as compared to a control carried out in the absence of said compound; or (B) bringing said compound into contact with methionine synthase in the presence of homocysteine and of methyl tetraglutamate or its polyglutamate derivatives, of S-adenosylmethionine synthetase, of ATP and of Mg, and of cofactors, and measuring the reduction in the formation of S-adenosylmethionine, phosphate or pyrophosphate as compared to a control carried out in the absence of said compound;

wherein the methionine synthase is derived from a phytopathogenic fungus; and (C) identifying the compound that reduces enzymatic activity and/or reduces the formation of methionine as an inhibitor of methionine.

* * * * *

SEQUENCE LISTING

<160> NUMBER OF SEQ ID NOS: 20

-continued

<210> SEQ ID NO 1
<211> LENGTH: 6500
<212> TYPE: DNA
<213> ORGANISM: Magnaporthe grisea
<220> FEATURE:
<221> NAME/KEY: gene
<222> LOCATION: (1)..(6500)

<400> SEQUENCE: 1

```
ggaagaaatc actgcgaaca acacacatct tggcccctga agctaggcca gtcttgtcaa     60

gcagtggcaa cgatggtaaa agcgagcgtt ggaaggattt ggagctcgtc attcccaaga    120

gacaggatga caacctctat caggtatgtt tcatatctcc ctgacttttg aattatccgg    180

cctgggtata gcccctattg ctaacctgcg tctgttactt tcacagaacc tcgaggatga    240

ggagttgctc aagatatcgc agcagatagg gagtcatatg gatagtatgc aaggaaatct    300

acggcaggtt gatggaattc ttccagcgat ggaaataaca aaggccgcgc ttcacgatgt    360

gttattgaaa cactccacca agtgtgagga ggtactgctt ggataagcac gcctatacta    420

ggttgggcaa aaggaccaaa gaaggttcgt ttgatacttg agatgggggc agtaatgtta    480

tcgtatgaat aatgagtcac catgtaaacg attgacagtc tgcaatcgga ggctaacgtc    540

ttcggcttcg gcttgttgga aaatcagacg agttcggact ggcgagtggg ttctcacgag    600

attgaggcca atgcttgccc gaacagtcaa ccaatttact acttccagcg gtgctactta    660

ataatcgatg cgcgtttggg cctagcacga cgtcggggtg tttgttccat gtaaaaggca    720

agtgagctta tgttgtagtg tagggaagaa ctttgagctt accatccata caaaacaagg    780

caatacacgg gaggtttaaa attgccctgc aaactttga cctccggtaa actccaggtc    840

aatttaaacc tcgattgtag cgcaagattc gacatctctg tcgaacaagc tctgatttgt    900

cgggggtcca tgccggttgc catggcgccc gacccggcct ccgatcaacg gacagttcga    960

accacattgg atgatatcta ggctggactg cgtggtatac gagaccataa ctaatcagga   1020

atgaagcccc agccaggtac agtacatatt gcaacctaaa gcacacaagc tatggtaagt   1080

agtgggcata ccgggtccag ccgacgggtg agttttgctg ggaccctcct tgtcattttt   1140

attgcagtaa gatataggtg ggcatacaaa gtaaaagcgt gatttacggt acggtacgga   1200

gcaccctcgg tactctggtt tagttacctg caatgcgacg tgtcaccccg ttcgcgacgt   1260

ctaggcaagg tagcggtgtg atattgtaca gtgtgcttga tagttattgt aggagttgga   1320

cccacgtcaa aattcctctt cggtagcatt cgcaccaagc gattggcaga aaatgacggg   1380

attgggattg aaatttctct gcaaaacctt aaaccttgct gagcccctcc ctaatgttgc   1440

cccgcgctgt ttaagaggtc gaagcttcga actagagctc tctgcgcccc accgttgtgc   1500

ccctccacga gtcgccctac gctttcatca cactttcgac aaccgctcat cggagcagca   1560

ttggactctt gctccttttg cgaagcaatt cagcaccggg agaggcagcg cagtcagtca   1620

gctgaggtgt ttacgagctt gttggtacct ttcccaaagg agacaggtac cgaagcttgc   1680

aaagatacct cagacgcttg agatttcagt cgaaaccagg gtctgggccc cacaaaattt   1740

tgccgttttt cccctccttc tttccatatg aagtctgtcc tcccctccat cccgttcctc   1800

tttaccaaca gatttttcca ttccctttct catacttttc ttctgtctgc atacaagctg   1860

gcacaaggtg aggctctggg agaaaatagt gagtgacttg agctttcacc ctctccgggt   1920

tgtcgatgtc gaattgctag tctaacttct gcgattccca tttattccca gtcaccgaag   1980

ccgtccaact cataacaaca ctcacattga gctcctaaaa tcgccggcga aaattcacac   2040

ttgagcaaaa tggttcaatc agcgattctc ggtttccccc gcatgggtgt gaaccgtgac   2100
```

-continued

```
ctgaagaagg ccactgaagc ttgtatgtct tgtcatcact gcaaaccacc aaggtctggc   2160
tccggatgat cgctgctaac accaattatc tgttagactg ggccggcaag atctcgcagg   2220
acgacctcct tgccgaggct aagaggctca gactcgccca ctggaagatc cagaaggatg   2280
ccggtgtcga catcatcccc agcaatgatt ttgctttgta cgaccaggtc ctttcacaca   2340
tccaggactt cggtgtgagt accatgccat cgagagcttt agtactttag ggatagccag   2400
ctgacacatt ggtaatgtat taggccgttc ccgaaaggta ctcaagctcc aagctgaacc   2460
ccgtcgacga gtacttcgcc atgggtcgtg gtcaccagaa ggatggtgtc gatgttccca   2520
gcttggagat ggtcaagtgg ttcgactcaa actaccacta cgtcaagccc actctccagg   2580
acaaccagac cttcacgctt acggccaacc ccaaggctgt gaatgagttc aacgaggcca   2640
aggaggctgg catcaacacc cgccccgtcc tcgttggtcc cgtttctttc cttcacctcg   2700
ccaaggctga ccgtggtcag tctgttgacc ccatcgacct ccttgacaag cttgtccccg   2760
tttacgagga gctcctcgcc aagctcaagg ccgctggtgc cgagactgtc cagattgacg   2820
agcctgtcct cgtcttcgac cttcccgcca aggtcaaggc tgctttcaag cccacatatg   2880
agaagtttgc cagcctgggt gacaagatcc ccaagctcgt tttcgccaca tacttcggtg   2940
acatcgtcca caatcttgac ctcgtcccca aggacgtcta cgccgtccac gtcgacctcg   3000
tcaggaaccc tgagcagttg gaaactgttg ttggtgccct gggccccaag accattcttt   3060
ctgctggtat cgtcgatggc cgtaacatct ggaagaccaa cttccagaag gccattgaga   3120
ctgttgagag tgcgatccag aagctcggca aggagcgtgt cattgttgcc acttccagct   3180
ctctccttca cactccccac acactagcga gcgagaagaa gcttgaccct gaaatcgccg   3240
actggttctc atttgcctct gagaaggccg tcgaggttgc catcatcgcc aaggccgtca   3300
ctgagggccc tgctgctgtc cgcgagcagc tcgaggccaa cgccaagtcg atgaacgctc   3360
gcgccacctc gagcagaaca aatgacccca aggtcaagga gaggcagtca aagattgtcg   3420
agtcagacta caaccgcaag tcggagttcc ctacccgtat ttcgcagcag caggccaagc   3480
ttaaccttcc tctctttccc actactacca tcgggtcctt cccccagacc cagactatcc   3540
gcgcccagcg tgccaagctc accaagaagg aaattgacgc tgagcaatac gccaagttca   3600
tcgaggagga gattgagaac aatgtaaaga tccaggaaga gctcggtctg gatgtcttcg   3660
tccacggtga gcccgagcgt aacgacatgg tgcaattctt tggtgagcgc ctggacggtt   3720
atgccttcac cacgcacgcc tgggttcaga gctacggttc ccgctgcgtc cgtcctccca   3780
tcattgtcgg tgacatctct cgcccggcac cgatgactgt caaggaatca aggtacgctg   3840
tcgagatttc caagaagccc atgaagggta tgttgacggg ccccgtcacc tgcctgaggt   3900
ggtcgttccc ccgtgacgat gtgcaccagt ccgtccaagc tgagcagctc gctcttgctc   3960
tccgtgacga ggttgttgac cttgagaagg ctggtgtcga cgtcatccag gtcgacgagc   4020
ctgctctccg tgagggtctg cccctccgct ctggtaagga gcgcgatgct tacctccagt   4080
gggctgtcaa ggctttcaag ctctcgacct gtggtgtcga ggactcgact cagatccact   4140
cgcacttctg ctactctgag ttccaggact tcttccacgc cattgctgcc cttgatgccg   4200
acgttctgtc catcgagaac agcaagtctg atgccaagct gctgaaggtg ttcgtcgact   4260
cggcttaccc ccgccacatc ggccccggtg tctacgacat ccactccccc cgtgttccca   4320
gcgaacagga gatcaaggac cgcatcgagg agatgcttca gtacctcaag cctgagcagc   4380
tctggatcga ccctgactgc ggtctgaaga cccgccagtg gaaggagacc aaggaggctc   4440
tcaccaacat ggtcaacgcc gccaagtact tccgtgccaa gtacgccaaa taagctgcaa   4500
```

-continued

```
gtcggctttt ttctttctct aatgttttac tcatctggtt tttcggcgtt tttgagccca   4560

cgcgtttccg tggcatgact tgcgggatct ggtcttcgat ttcaacatcg gcgttttttt   4620

tttcttgatt ctgggatatg atatcaaaag tgcaagcgat aagtctccga aatacaggtg   4680

ttcgggtggg tttaaaaact ggtggttggg ttcatgggaa cggcgtgagg atcattcaac   4740

atttggcaag gaataccaaa agggttccgg agacctagag ggaattttgt ccatcaaccg   4800

gacttcccga atcactcata cccctattct atttcctttt tcccttttt tttgtttttg    4860

gtacgaagtc ctttttcatc ttcttgcaac ataccatcag atataatgac gggagtattg   4920

gggcagagaa gtaggaaggg ccactgatgt cagtacagac tgaccgtggc agttagatag   4980

tcacactata ggaatgaatg agacccaatt caactgggta atagactgtc ctggacttgg   5040

cttttttcc ttggggcatt attatcaagc agccactttc agtagtaaac aaatactctg    5100

gggttccacc actataatac agatggagat actcaagtac ttgaactttt acataaactc   5160

gttccattac gtggaacccc aaaacgacga ccaaacgaca ctccaaccta tttacctaca   5220

caggtctacc gacctaccct tttgatagat acttgtgctg tttgtccaaa cttggctatt   5280

tttacggcta ctatgtactc ggtgcggacg cggactgtat atggtaaatg tggctgctga   5340

ctactgaaat tagctaattg atgagagcac cctttttcaa acgttataga actgagataa   5400

tgggttttta tttaccaccc gaattcgaga cacagggtaa gtccgtaata ggaaacccca   5460

gaaacttacc caccaggtac ctatcctacc aagtcgctca tcggtctaaa tacctactca   5520

cccggtacct atctattgtt tataagtgtg cagggctcca atgcgtaggc atgttcccaa   5580

cgttagcaat gggcaagcca acttttaggt gggttctatc acgtcgcctt gtttaaagtg   5640

aaatgtagat caacatgtct tggagagtcc gaaactgtgg ttgaaagacg gacaattctc   5700

cgatgttgcg ggaggatcgt acaaagtaaa agcacctgat tcctggagct gtaaatggga   5760

gtcaggacgt tttgcaagga aaagggttgt tgttgttgtt tgtgtctagg aagcgaatat   5820

tcaggggtgg aaggtcgaat attacagatc cgcccagtgt ttggaggatc tggacttcgc   5880

ctagcaggag gagccatgcg cagtgggggc aatgcctgtt gtgaaacggc ctggtgatga   5940

acaactgccc cacgcgttga ggagagagag tcctttttcg tctttatcac cggttcgcgt   6000

gggaaaaggt ggagaaacag ctcgcacctg gaccgacctt gagcaaggag cacgcagtat   6060

gtcacaattg atctcaaaca cacatcattt ccgaagaatt gccagtggta tatctcttgc   6120

tgcacaacag atggagattc gatcacggtg tgtaagagga ttatcaacat agccacttta   6180

tcatagcaat attcaatgca cctatatcgc accgggtgat ttggatccag gggagctagc   6240

attgctggga acggagcctc cagtcttttt ggtccttgtt gccagccttt tttttcgtct   6300

cttttcgtca ttcatcgctt tctcttcccg gaaaagcatc gaagaatgta cagtagtatg   6360

cgggagtaga tggtaggacg gcatctccgc agagacatcg gcagccaagt aggttgtgga   6420

tatccatcga tcttcgttac tttttctgga agctctccat atcaagcggt actgtagtgt   6480

ttttttttct tttcttttct                                               6500
```

```
<210> SEQ ID NO 2
<211> LENGTH: 2301
<212> TYPE: DNA
<213> ORGANISM: Magnaporthe grisea
<220> FEATURE:
<221> NAME/KEY: CDS
<222> LOCATION: (1)..(2301)

<400> SEQUENCE: 2

atg gtt caa tca gcg att ctc ggt ttc ccc cgc atg ggt gtg aac cgt       48
```

-continued

```
Met Val Gln Ser Ala Ile Leu Gly Phe Pro Arg Met Gly Val Asn Arg
1               5                   10                  15

gac ctg aag aag gcc act gaa gct tac tgg gcc ggc aag atc tcg cag       96
Asp Leu Lys Lys Ala Thr Glu Ala Tyr Trp Ala Gly Lys Ile Ser Gln
            20                  25                  30

gac gac ctc ctt gcc gag gct aag agg ctc aga ctc gcc cac tgg aag      144
Asp Asp Leu Leu Ala Glu Ala Lys Arg Leu Arg Leu Ala His Trp Lys
        35                  40                  45

atc cag aag gat gcc ggt gtc gac atc atc ccc agc aat gat ttt gct      192
Ile Gln Lys Asp Ala Gly Val Asp Ile Ile Pro Ser Asn Asp Phe Ala
    50                  55                  60

ttg tac gac cag gtc ctt tca cac atc cag gac ttc ggt gcc gtt ccc      240
Leu Tyr Asp Gln Val Leu Ser His Ile Gln Asp Phe Gly Ala Val Pro
65                  70                  75                  80

gaa agg tac tca agc tcc aag ctg aac ccc gtc gac gag tac ttc gcc      288
Glu Arg Tyr Ser Ser Ser Lys Leu Asn Pro Val Asp Glu Tyr Phe Ala
                85                  90                  95

atg ggt cgt ggt cac cag aag gat ggt gtc gat gtt ccc agc ttg gag      336
Met Gly Arg Gly His Gln Lys Asp Gly Val Asp Val Pro Ser Leu Glu
            100                 105                 110

atg gtc aag tgg ttc gac tca aac tac cac tac gtc aag ccc act ctc      384
Met Val Lys Trp Phe Asp Ser Asn Tyr His Tyr Val Lys Pro Thr Leu
        115                 120                 125

cag gac aac cag acc ttc acg ctt acg gcc aac ccc aag gct gtg aat      432
Gln Asp Asn Gln Thr Phe Thr Leu Thr Ala Asn Pro Lys Ala Val Asn
    130                 135                 140

gag ttc aac gag gcc aag gag gct ggc atc aac acc cgc ccc gtc ctc      480
Glu Phe Asn Glu Ala Lys Glu Ala Gly Ile Asn Thr Arg Pro Val Leu
145                 150                 155                 160

gtt ggt ccc gtt tct ttc ctt cac ctc gcc aag gct gac cgt ggt cag      528
Val Gly Pro Val Ser Phe Leu His Leu Ala Lys Ala Asp Arg Gly Gln
                165                 170                 175

tct gtt gac ccc atc gac ctc ctt gac aag ctt gtc ccc gtt tac gag      576
Ser Val Asp Pro Ile Asp Leu Leu Asp Lys Leu Val Pro Val Tyr Glu
            180                 185                 190

gag ctc ctc gcc aag ctc aag gcc gct ggt gcc gag act gtc cag att      624
Glu Leu Leu Ala Lys Leu Lys Ala Ala Gly Ala Glu Thr Val Gln Ile
        195                 200                 205

gac gag cct gtc ctc gtc ttc gac ctt ccc gcc aag gtc aag gct gct      672
Asp Glu Pro Val Leu Val Phe Asp Leu Pro Ala Lys Val Lys Ala Ala
    210                 215                 220

ttc aag ccc aca tat gag aag ttt gcc agc ctg ggt gac aag atc ccc      720
Phe Lys Pro Thr Tyr Glu Lys Phe Ala Ser Leu Gly Asp Lys Ile Pro
225                 230                 235                 240

aag ctc gtt ttc gcc aca tac ttc ggt gac atc gtc cac aat ctt gac      768
Lys Leu Val Phe Ala Thr Tyr Phe Gly Asp Ile Val His Asn Leu Asp
                245                 250                 255

ctc gtc ccc aag gac gtc tac gcc gtc cac gtc gac ctc gtc agg aac      816
Leu Val Pro Lys Asp Val Tyr Ala Val His Val Asp Leu Val Arg Asn
            260                 265                 270

cct gag cag ttg gaa act gtt gtt ggt gcc ctg ggc ccc aag acc att      864
Pro Glu Gln Leu Glu Thr Val Val Gly Ala Leu Gly Pro Lys Thr Ile
        275                 280                 285

ctt tct gct ggt atc gtc gat ggc cgt aac atc tgg aag acc aac ttc      912
Leu Ser Ala Gly Ile Val Asp Gly Arg Asn Ile Trp Lys Thr Asn Phe
    290                 295                 300

cag aag gcc att gag act gtt gag agt gcg atc cag aag ctc ggc aag      960
Gln Lys Ala Ile Glu Thr Val Glu Ser Ala Ile Gln Lys Leu Gly Lys
305                 310                 315                 320

gag cgt gtc att gtt gcc act tcc agc tct ctc ctt cac act ccc cac     1008
```

-continued

```
Glu Arg Val Ile Val Ala Thr Ser Ser Ser Leu Leu His Thr Pro His
                325                 330                 335

aca cta gcg agc gag aag aag ctt gac cct gaa atc gcc gac tgg ttc     1056
Thr Leu Ala Ser Glu Lys Lys Leu Asp Pro Glu Ile Ala Asp Trp Phe
            340                 345                 350

tca ttt gcc tct gag aag gcc gtc gag gtt gcc atc atc gcc aag gcc     1104
Ser Phe Ala Ser Glu Lys Ala Val Glu Val Ala Ile Ile Ala Lys Ala
        355                 360                 365

gtc act gag ggc cct gct gct gtc cgc gag cag ctc gag gcc aac gcc     1152
Val Thr Glu Gly Pro Ala Ala Val Arg Glu Gln Leu Glu Ala Asn Ala
    370                 375                 380

aag tcg atg aac gct cgc gcc acc tcg agc aga aca aat gac ccc aag     1200
Lys Ser Met Asn Ala Arg Ala Thr Ser Ser Arg Thr Asn Asp Pro Lys
385                 390                 395                 400

gtc aag gag agg cag tca aag att gtc gag tca gac tac aac cgc aag     1248
Val Lys Glu Arg Gln Ser Lys Ile Val Glu Ser Asp Tyr Asn Arg Lys
                405                 410                 415

tcg gag ttc cct acc cgt att tcg cag cag cag gcc aag ctt aac ctt     1296
Ser Glu Phe Pro Thr Arg Ile Ser Gln Gln Gln Ala Lys Leu Asn Leu
            420                 425                 430

cct ctc ttt ccc act act acc atc ggg tcc ttc ccc cag acc cag act     1344
Pro Leu Phe Pro Thr Thr Thr Ile Gly Ser Phe Pro Gln Thr Gln Thr
        435                 440                 445

atc cgc gcc cag cgt gcc aag ctc acc aag aag gaa att gac gct gag     1392
Ile Arg Ala Gln Arg Ala Lys Leu Thr Lys Lys Glu Ile Asp Ala Glu
    450                 455                 460

caa tac gcc aag ttc atc gag gag gag att gag aac aat gta aag atc     1440
Gln Tyr Ala Lys Phe Ile Glu Glu Glu Ile Glu Asn Asn Val Lys Ile
465                 470                 475                 480

cag gaa gag ctc ggt ctg gat gtc ttc gtc cac ggt gag ccc gag cgt     1488
Gln Glu Glu Leu Gly Leu Asp Val Phe Val His Gly Glu Pro Glu Arg
                485                 490                 495

aac gac atg gtg caa ttc ttt ggt gag cgc ctg gac ggt tat gcc ttc     1536
Asn Asp Met Val Gln Phe Phe Gly Glu Arg Leu Asp Gly Tyr Ala Phe
            500                 505                 510

acc acg cac gcc tgg gtt cag agc tac ggt tcc cgc tgc gtc cgt cct     1584
Thr Thr His Ala Trp Val Gln Ser Tyr Gly Ser Arg Cys Val Arg Pro
        515                 520                 525

ccc atc att gtc ggt gac atc tct cgc ccg gca ccg atg act gtc aag     1632
Pro Ile Ile Val Gly Asp Ile Ser Arg Pro Ala Pro Met Thr Val Lys
    530                 535                 540

gaa tca agg tac gct gtc gag att tcc aag aag ccc atg aag ggt atg     1680
Glu Ser Arg Tyr Ala Val Glu Ile Ser Lys Lys Pro Met Lys Gly Met
545                 550                 555                 560

ttg acg ggc ccc gtc acc tgc ctg agg tgg tcg ttc ccc cgt gac gat     1728
Leu Thr Gly Pro Val Thr Cys Leu Arg Trp Ser Phe Pro Arg Asp Asp
                565                 570                 575

gtg cac cag tcc gtc caa gct gag cag ctc gct ctt gct ctc cgt gac     1776
Val His Gln Ser Val Gln Ala Glu Gln Leu Ala Leu Ala Leu Arg Asp
            580                 585                 590

gag gtt gtt gac ctt gag aag gct ggt gtc gac gtc atc cag gtc gac     1824
Glu Val Val Asp Leu Glu Lys Ala Gly Val Asp Val Ile Gln Val Asp
        595                 600                 605

gag cct gct ctc cgt gag ggt ctg ccc ctc cgc tct ggt aag gag cgc     1872
Glu Pro Ala Leu Arg Glu Gly Leu Pro Leu Arg Ser Gly Lys Glu Arg
    610                 615                 620

gat gct tac ctc cag tgg gct gtc aag gct ttc aag ctc tcg acc tgt     1920
Asp Ala Tyr Leu Gln Trp Ala Val Lys Ala Phe Lys Leu Ser Thr Cys
625                 630                 635                 640

ggt gtc gag gac tcg act cag atc cac tcg cac ttc tgc tac tct gag     1968
```

```
Gly Val Glu Asp Ser Thr Gln Ile His Ser His Phe Cys Tyr Ser Glu
                645                 650                 655

ttc cag gac ttc ttc cac gcc att gct gcc ctt gat gcc gac gtt ctg      2016
Phe Gln Asp Phe Phe His Ala Ile Ala Ala Leu Asp Ala Asp Val Leu
            660                 665                 670

tcc atc gag aac agc aag tct gat gcc aag ctg ctg aag gtg ttc gtc      2064
Ser Ile Glu Asn Ser Lys Ser Asp Ala Lys Leu Leu Lys Val Phe Val
        675                 680                 685

gac tcg gct tac ccc cgc cac atc ggc ccc ggt gtc tac gac atc cac      2112
Asp Ser Ala Tyr Pro Arg His Ile Gly Pro Gly Val Tyr Asp Ile His
    690                 695                 700

tcc ccc cgt gtt ccc agc gaa cag gag atc aag gac cgc atc gag gag      2160
Ser Pro Arg Val Pro Ser Glu Gln Glu Ile Lys Asp Arg Ile Glu Glu
705                 710                 715                 720

atg ctt cag tac ctc aag cct gag cag ctc tgg atc gac cct gac tgc      2208
Met Leu Gln Tyr Leu Lys Pro Glu Gln Leu Trp Ile Asp Pro Asp Cys
                725                 730                 735

ggt ctg aag acc cgc cag tgg aag gag acc aag gag gct ctc acc aac      2256
Gly Leu Lys Thr Arg Gln Trp Lys Glu Thr Lys Glu Ala Leu Thr Asn
            740                 745                 750

atg gtc aac gcc gcc aag tac ttc cgt gcc aag tac gcc aaa taa          2301
Met Val Asn Ala Ala Lys Tyr Phe Arg Ala Lys Tyr Ala Lys
        755                 760                 765


<210> SEQ ID NO 3
<211> LENGTH: 766
<212> TYPE: PRT
<213> ORGANISM: Magnaporthe grisea

<400> SEQUENCE: 3

Met Val Gln Ser Ala Ile Leu Gly Phe Pro Arg Met Gly Val Asn Arg
1               5                   10                  15

Asp Leu Lys Lys Ala Thr Glu Ala Tyr Trp Ala Gly Lys Ile Ser Gln
            20                  25                  30

Asp Asp Leu Leu Ala Glu Ala Lys Arg Leu Arg Leu Ala His Trp Lys
        35                  40                  45

Ile Gln Lys Asp Ala Gly Val Asp Ile Ile Pro Ser Asn Asp Phe Ala
    50                  55                  60

Leu Tyr Asp Gln Val Leu Ser His Ile Gln Asp Phe Gly Ala Val Pro
65                  70                  75                  80

Glu Arg Tyr Ser Ser Ser Lys Leu Asn Pro Val Asp Glu Tyr Phe Ala
                85                  90                  95

Met Gly Arg Gly His Gln Lys Asp Gly Val Asp Val Pro Ser Leu Glu
            100                 105                 110

Met Val Lys Trp Phe Asp Ser Asn Tyr His Tyr Val Lys Pro Thr Leu
        115                 120                 125

Gln Asp Asn Gln Thr Phe Thr Leu Thr Ala Asn Pro Lys Ala Val Asn
    130                 135                 140

Glu Phe Asn Glu Ala Lys Glu Ala Gly Ile Asn Thr Arg Pro Val Leu
145                 150                 155                 160

Val Gly Pro Val Ser Phe Leu His Leu Ala Lys Ala Asp Arg Gly Gln
                165                 170                 175

Ser Val Asp Pro Ile Asp Leu Leu Asp Lys Leu Val Pro Val Tyr Glu
            180                 185                 190

Glu Leu Leu Ala Lys Leu Lys Ala Ala Gly Ala Glu Thr Val Gln Ile
        195                 200                 205

Asp Glu Pro Val Leu Val Phe Asp Leu Pro Ala Lys Val Lys Ala Ala
    210                 215                 220
```

-continued

```
Phe Lys Pro Thr Tyr Glu Lys Phe Ala Ser Leu Gly Asp Lys Ile Pro
225                 230                 235                 240

Lys Leu Val Phe Ala Thr Tyr Phe Gly Asp Ile Val His Asn Leu Asp
                245                 250                 255

Leu Val Pro Lys Asp Val Tyr Ala Val His Val Asp Leu Val Arg Asn
            260                 265                 270

Pro Glu Gln Leu Glu Thr Val Val Gly Ala Leu Gly Pro Lys Thr Ile
        275                 280                 285

Leu Ser Ala Gly Ile Val Asp Gly Arg Asn Ile Trp Lys Thr Asn Phe
    290                 295                 300

Gln Lys Ala Ile Glu Thr Val Glu Ser Ala Ile Gln Lys Leu Gly Lys
305                 310                 315                 320

Glu Arg Val Ile Val Ala Thr Ser Ser Ser Leu Leu His Thr Pro His
                325                 330                 335

Thr Leu Ala Ser Glu Lys Lys Leu Asp Pro Glu Ile Ala Asp Trp Phe
            340                 345                 350

Ser Phe Ala Ser Glu Lys Ala Val Glu Val Ala Ile Ile Ala Lys Ala
        355                 360                 365

Val Thr Glu Gly Pro Ala Ala Val Arg Glu Gln Leu Glu Ala Asn Ala
    370                 375                 380

Lys Ser Met Asn Ala Arg Ala Thr Ser Ser Arg Thr Asn Asp Pro Lys
385                 390                 395                 400

Val Lys Glu Arg Gln Ser Lys Ile Val Glu Ser Asp Tyr Asn Arg Lys
                405                 410                 415

Ser Glu Phe Pro Thr Arg Ile Ser Gln Gln Gln Ala Lys Leu Asn Leu
            420                 425                 430

Pro Leu Phe Pro Thr Thr Thr Ile Gly Ser Phe Pro Gln Thr Gln Thr
        435                 440                 445

Ile Arg Ala Gln Arg Ala Lys Leu Thr Lys Lys Glu Ile Asp Ala Glu
    450                 455                 460

Gln Tyr Ala Lys Phe Ile Glu Glu Glu Ile Glu Asn Asn Val Lys Ile
465                 470                 475                 480

Gln Glu Glu Leu Gly Leu Asp Val Phe Val His Gly Glu Pro Glu Arg
                485                 490                 495

Asn Asp Met Val Gln Phe Phe Gly Glu Arg Leu Asp Gly Tyr Ala Phe
            500                 505                 510

Thr Thr His Ala Trp Val Gln Ser Tyr Gly Ser Arg Cys Val Arg Pro
        515                 520                 525

Pro Ile Ile Val Gly Asp Ile Ser Arg Pro Ala Pro Met Thr Val Lys
    530                 535                 540

Glu Ser Arg Tyr Ala Val Glu Ile Ser Lys Lys Pro Met Lys Gly Met
545                 550                 555                 560

Leu Thr Gly Pro Val Thr Cys Leu Arg Trp Ser Phe Pro Arg Asp Asp
                565                 570                 575

Val His Gln Ser Val Gln Ala Glu Gln Leu Ala Leu Ala Leu Arg Asp
            580                 585                 590

Glu Val Val Asp Leu Glu Lys Ala Gly Val Asp Val Ile Gln Val Asp
        595                 600                 605

Glu Pro Ala Leu Arg Glu Gly Leu Pro Leu Arg Ser Gly Lys Glu Arg
    610                 615                 620

Asp Ala Tyr Leu Gln Trp Ala Val Lys Ala Phe Lys Leu Ser Thr Cys
625                 630                 635                 640

Gly Val Glu Asp Ser Thr Gln Ile His Ser His Phe Cys Tyr Ser Glu
```

-continued

```
                645                 650                 655

Phe Gln Asp Phe Phe His Ala Ile Ala Ala Leu Asp Ala Asp Val Leu
            660                 665                 670

Ser Ile Glu Asn Ser Lys Ser Asp Ala Lys Leu Leu Lys Val Phe Val
        675                 680                 685

Asp Ser Ala Tyr Pro Arg His Ile Gly Pro Gly Val Tyr Asp Ile His
    690                 695                 700

Ser Pro Arg Val Pro Ser Glu Gln Glu Ile Lys Asp Arg Ile Glu Glu
705                 710                 715                 720

Met Leu Gln Tyr Leu Lys Pro Glu Gln Leu Trp Ile Asp Pro Asp Cys
                725                 730                 735

Gly Leu Lys Thr Arg Gln Trp Lys Glu Thr Lys Glu Ala Leu Thr Asn
            740                 745                 750

Met Val Asn Ala Ala Lys Tyr Phe Arg Ala Lys Tyr Ala Lys
        755                 760                 765


<210> SEQ ID NO 4
<211> LENGTH: 20
<212> TYPE: DNA
<213> ORGANISM: Artificial
<220> FEATURE:
<223> OTHER INFORMATION: PCR primer
<220> FEATURE:
<221> NAME/KEY: primer
<222> LOCATION: (1)..(20)

<400> SEQUENCE: 4

gacagtctgc aatcggaggc                                                   20


<210> SEQ ID NO 5
<211> LENGTH: 21
<212> TYPE: DNA
<213> ORGANISM: Artificial
<220> FEATURE:
<223> OTHER INFORMATION: PCR primer
<220> FEATURE:
<221> NAME/KEY: primer
<222> LOCATION: (1)..(20)

<400> SEQUENCE: 5

gcatggctcc tcctgctagg c                                                 21


<210> SEQ ID NO 6
<211> LENGTH: 20
<212> TYPE: DNA
<213> ORGANISM: Artificial
<220> FEATURE:
<223> OTHER INFORMATION: PCR primer
<220> FEATURE:
<221> NAME/KEY: primer
<222> LOCATION: (1)..(20)

<400> SEQUENCE: 6

tagagtagat gccgaccggg                                                   20


<210> SEQ ID NO 7
<211> LENGTH: 20
<212> TYPE: DNA
<213> ORGANISM: Artificial
<220> FEATURE:
<223> OTHER INFORMATION: PCR primer
<220> FEATURE:
<221> NAME/KEY: primer
<222> LOCATION: (1)..(20)

<400> SEQUENCE: 7
```

ggctccgttc ccagcaatgc 20

<210> SEQ ID NO 8
<211> LENGTH: 20
<212> TYPE: DNA
<213> ORGANISM: Artificial
<220> FEATURE:
<223> OTHER INFORMATION: PCR primer
<220> FEATURE:
<221> NAME/KEY: primer
<222> LOCATION: (1)..(20)

<400> SEQUENCE: 8
ggagttgctc aagatatcgc 20

<210> SEQ ID NO 9
<211> LENGTH: 24
<212> TYPE: DNA
<213> ORGANISM: Artificial
<220> FEATURE:
<223> OTHER INFORMATION: PCR primer

<400> SEQUENCE: 9
aggctctcgc tgaactcccc aatg 24

<210> SEQ ID NO 10
<211> LENGTH: 20
<212> TYPE: DNA
<213> ORGANISM: Artificial
<220> FEATURE:
<223> OTHER INFORMATION: PCR primer

<400> SEQUENCE: 10
ggttcaatca gcgattctcg 20

<210> SEQ ID NO 11
<211> LENGTH: 20
<212> TYPE: DNA
<213> ORGANISM: Artificial
<220> FEATURE:
<223> OTHER INFORMATION: PCR primer
<220> FEATURE:
<221> NAME/KEY: primer
<222> LOCATION: (1)..(20)

<400> SEQUENCE: 11
gcttatttgg cgtacttggc 20

<210> SEQ ID NO 12
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: primer
<222> LOCATION: (1)..(30)

<400> SEQUENCE: 12
ccggaattct gacagtctgc aatcggaggc 30

<210> SEQ ID NO 13
<211> LENGTH: 30
<212> TYPE: DNA
<213> ORGANISM: Artificial
<220> FEATURE:
<223> OTHER INFORMATION: PCR primer
<220> FEATURE:

<221> NAME/KEY: primer
<222> LOCATION: (1)..(30)

<400> SEQUENCE: 13
tccccgcggt ggacggcttc ggtgactggg 30

<210> SEQ ID NO 14
<211> LENGTH: 30
<212> TYPE: DNA
<213> ORGANISM: Artificial
<220> FEATURE:
<223> OTHER INFORMATION: PCR primer

<400> SEQUENCE: 14
ggaagatcta gtgcaagcga taagtctccg 30

<210> SEQ ID NO 15
<211> LENGTH: 30
<212> TYPE: DNA
<213> ORGANISM: Artificial
<220> FEATURE:
<223> OTHER INFORMATION: PCR primer

<400> SEQUENCE: 15
gcgggatccg catggctcct cctgctaggc 30

<210> SEQ ID NO 16
<211> LENGTH: 4570
<212> TYPE: DNA
<213> ORGANISM: Ustilago maydis
<220> FEATURE:
<221> NAME/KEY: gene
<222> LOCATION: (1)..(4570)

<400> SEQUENCE: 16
tcttgcgttg tatgttgatg atgagcgtgt tccgagaaga acaaatcgag ctatctacgg 60
tctctctgta tttcaccgct gaagtccaag tacaggcttg tactgtgata actaggctgt 120
gcgctgcagt gcatgcgtgt gaaccaacac aggctggcca cgcttgtgtg ccctgtgcat 180
gtgtgtgtct gccgaatcac gaatgctaaa tgcatgtgat tttccagaaa agtgtcactt 240
tccgaataat cacaaggacg cgcctcttgc tgacataatc aagttcaagg aaattaaagt 300
taagtcacaa gtcacagtca cgagtgcgag ccgccgaaag cggccaaaca catgtcatcg 360
ttcataacta gtttccttca cgcacgagtt aaatcaggct tgtagatggc attatccatg 420
ttgaaatctg gaattgctag gatcatgttg aatgcttttg aggcgggata tcatgttgaa 480
tgcttacaga atacagaggt ggaatacgag aaacagatgc gaggagagag aaagaaaaag 540
acaatgacga caatagaggg agaccataaa ctcatactag tgggagatgg gaggggatag 600
agctgcactc ggcgtagacc aaagcagttg atgctggatc catgggcacg agaagagctt 660
gttcaagctg gggtgatatg gaaagagaat tttaagcaag ggtctggcgg cactcctcag 720
cggcagcaac catgttggtg agctgggcag tgcactcctc ccaggttcgg gtcttgagac 780
cacagtcggg gttgacccag atcgagtcct tgggaagcac ctcggccatg gccttgatgc 840
ggcccaccat ctcgtccttg ctgggcacac ggggcgagtg gatgtcaaag acaccagggc 900
caatgtgcga ggggtagcca accttcttga aggcaccgag aaggtgctca ccggacttgg 960
agtgctcaat cgagatcata tcggcatcga gctcgatgat cgacttcata atgagcgaga 1020
agtccgagta gcagaagtgc gaggcgatgt tcatggcgtc cgagcaaccc gaagtggaga 1080
gacggaacga gtcgacagcc catcgcaggt aaccagccca gtccttctgg cggagcggca 1140

-continued

```
gaccctcacg aatggcgggc tcgtcgacct gaacggcacg aacaccggcc ttctcgaggt   1200
cgatgacctc gtcgcggagg gcgagggcga tctgcttgga ctgtacctcc ttgctgatgt   1260
cggcacgagg gaacgaccag ttgaggatgg tgacgggacc agtaagcata cccttcatgg   1320
gcttcttggt gaggctctga gcgtacgacg accagcgcac agtcatggga gcaggacggc   1380
tgacgtccga gacgacaacg gggggacgaa cgtatcgcga accgaacgac tggacccagg   1440
cgttctgggt gaagacgaaa ccgtcgagca gctcaccgaa gtactggacc atgtcgttac   1500
gctcgggctc accgtgaacg agcacgtcga ggttgagggc ctcctgcttc tcgacgacca   1560
tcttgatctc gtcttcgagg aacttttcgt actcctcctt ggtgatctcg gacttgttga   1620
aacgcgcacg gtactgacgg atctccttgg tctgggggaa agagccgatg gtggtggtgg   1680
ggaagatggg gagcgcaagg tgctccttct gaacctcctt tcgcacgttg aaaggcgact   1740
tgcgggcgag gtcctcctcc ttgatgttgg caacgcgttc acgaacggcg gggtcagagt   1800
tcttctcaaa gtcgcgacgg gccttgatgc tcttctcgtt gacggcgaga gcgtcggcgg   1860
ccgagcttgg gtcgcggaga gcagcagcga gggtggcaat ctcagcacac ttctcgttgg   1920
cgaacgagaa ccagtcgagc acctcagcgc tcagcttctt ctcgttggcg atggtgatgg   1980
gggtgtggag gagcgaggac gaagaagcaa tctgaacacg cgaagcgtcg ccgagcttct   2040
cgacggcctt ctgggcaatc ttgagggcag cgctgaggtc agttttccag atgttacggc   2100
cggagacgag accgagcgag acgacgtgct tggtgttaac gaaggcggcg aggacctcgt   2160
cgagctgctc aggagcacgg tcaagatcga tgtggagacc agcgacgggg agggtcttga   2220
cgatctcgag gttggactcg agcttgttga agtaggtagc aatcatgatc ttgaccgagg   2280
gggcagcctg agcgatggtc tcgtaggcgg ccttgaactc ggcggcgtac tgctgggcac   2340
ggtcaagaac gaggacgggc tcatcaatct ggacccactc ggcaccggcc tcgccgagtt   2400
tggcgagcaa ttcaccgtag acgggggcaa gcttgctgag gagcgagacg gggtcgagct   2460
cggcgtcctt ggcgtccttg ccgggcttac caagggcgag gagggtgacg ggaccgacga   2520
ggacggggcg ggcgttgtag ccggcctcct tggcctcaac aaagtcgtcg atgggcttgg   2580
tgttgttaat cttgaactcg gtggactcgc tcagttcggg gacgaggtag tggtagttcg   2640
agtcgaacca cttctgcatt tcggtggcgg gaaggtcgac accgttcttc tggtggccac   2700
gggccatggc gaagtaggtg tcgagagcat caaggccaga cttggcgtag ttctctggaa   2760
taaggttgaa ggtgttggag gcgtccagga cgtggtcgta gagcgagaag gtaccggtgg   2820
gcacaacatc gacaccagca tccttgatga acttgtaggt ctggagacgc tgctccttgg   2880
cgaccttgag gagctcctcc tgggaagact tacctcccca gtaggcctca agagccttct   2940
tgacctcacg ctgaggacca atgcgggggt aaccgaggac ggcggaagta ctgtgagtgt   3000
cgagagggag aatagaaata atcagcgaat tgtcttgaaa tcaatgacac gatcatgatg   3060
agccatgtgc ggttggtact tacgccattt taaatatatg agaggaacga acgaataagg   3120
gaaagggaat gatagcgaga gacgtctaga acagaggatt cagacgacag tgaacaaact   3180
tctcgggtcg tggatacgag caagaagtga gaaagaagcg gagatggagg atggtggttg   3240
ggtgggatgg atgatgtagg aggaagggaa gaaggaaggg gtacttgcgc caggaagaag   3300
aaataggaat tggcgagcgt gcgaaccatc acttctatgt ggtgtcgtgc tagggcccgg   3360
tcaggaagga aatcctgcgt tcttctaacc tgtaggcgaa tgagggcgtg cggtagacgt   3420
tgggcagctg cacagtcgcc actctggtag gcagaaaaag aacagcggct gttggcccaa   3480
gcgagcaacc taaatgggct gtcgtgcgtt gaggcagagc aaatgcgtgc tcttcgtaac   3540
```

-continued

```
cgcacgtttt catccaatcg acaagtgagc agatttttca cttttctgtt tgctgtcgtc   3600

ttttcttcca gctagctttt cctctgccaa cgtgcctgtc tcaatttttt ttcttgtgag   3660

ttctgctgcg ctcgcgttgt ggctgccttt ctttggcctt gacggaatct caagcgtttc   3720

agggtacact gagactgtga ccgtgactct ctgtgactta ggaaggtgtc gtctgccaac   3780

cagccctgca gctcccgtcc aaaaggcgtg atggcccaac caattcgagt cagtcacgag   3840

tgtgcgcccc aggtttttgc atcgcatctg atcttttcaa acgttctggt tggtcgagac   3900

ggctccatgt ctgcagcgcc gcgcggatca ttcacacttt gctatgatag gacaattgtg   3960

aatcactcgt gactgcaatc gttgattggt ccgaaaccct ctctctcatt cacgtacgaa   4020

tcgtgaagtg aatctgcacg tacagaagct cttcccctct cttctgttcg aagtctttgc   4080

tgaggctcct gttgccatca tcactacgat ggggaccgct ggtcgtgcca tctcgaggtg   4140

tagtaatagg gctgcccgta tgcatcacag atcagcttgt tgcctgaaca gcgcagcgac   4200

gttcgactca ggtgtctggg tcagcgtgcg ttggcagcct ctcgtgcacg tttatgtccc   4260

tgttcaactt gtcgagtcat gagcaaactc aggaccgaac atggaaaaat gctgctgttg   4320

ttggaataga gcgtctaaca atcacgaatg gaggcacagc tgctgcgtgt aggcagtcgt   4380

gagtcacgag tcgtgagtcg ttgagcctcg tgccttgagg tcacgagtaa cgtcatgttg   4440

tgttagaccc tggcaaagac gcgatttcaa tttcaatttc gacacctgtt gtccgtgcat   4500

tcacgattcg tgattgacgc tccttgacgt cttggctggt cactgcgtgt caaactgtga   4560

ctgagctaga                                                          4570


<210> SEQ ID NO 17
<211> LENGTH: 2304
<212> TYPE: DNA
<213> ORGANISM: Ustilago maydis
<220> FEATURE:
<221> NAME/KEY: CDS
<222> LOCATION: (1)..(2304)
<223> OTHER INFORMATION: cDNA

<400> SEQUENCE: 17

atg gct act tcc gcc gtc ctc ggt tac ccc cgc att ggt cct cag cgt       48
Met Ala Thr Ser Ala Val Leu Gly Tyr Pro Arg Ile Gly Pro Gln Arg
1               5                   10                  15

gag gtc aag aag gct ctt gag gcc tac tgg gga ggt aag tct tcc cag       96
Glu Val Lys Lys Ala Leu Glu Ala Tyr Trp Gly Gly Lys Ser Ser Gln
            20                  25                  30

gag gag ctc ctc aag gtc gcc aag gag cag cgt ctc cag acc tac aag      144
Glu Glu Leu Leu Lys Val Ala Lys Glu Gln Arg Leu Gln Thr Tyr Lys
        35                  40                  45

ttc atc aag gat gct ggt gtc gat gtt gtg ccc acc ggt acc ttc tcg      192
Phe Ile Lys Asp Ala Gly Val Asp Val Val Pro Thr Gly Thr Phe Ser
    50                  55                  60

ctc tac gac cac gtc ctg gac gcc tcc aac acc ttc aac ctt att cca      240
Leu Tyr Asp His Val Leu Asp Ala Ser Asn Thr Phe Asn Leu Ile Pro
65                  70                  75                  80

gag aac tac gcc aag tct ggc ctt gat gct ctc gac acc tac ttc gcc      288
Glu Asn Tyr Ala Lys Ser Gly Leu Asp Ala Leu Asp Thr Tyr Phe Ala
                85                  90                  95

atg gcc cgt ggc cac cag aag aac ggt gtc gac ctt ccc gcc acc gaa      336
Met Ala Arg Gly His Gln Lys Asn Gly Val Asp Leu Pro Ala Thr Glu
            100                 105                 110

atg cag aag tgg ttc gac tcg aac tac cac tac ctc gtc ccc gaa ctg      384
Met Gln Lys Trp Phe Asp Ser Asn Tyr His Tyr Leu Val Pro Glu Leu
        115                 120                 125
```

-continued

```
agc gag tcc acc gag ttc aag att aac aac acc aag ccc atc gac gac       432
Ser Glu Ser Thr Glu Phe Lys Ile Asn Asn Thr Lys Pro Ile Asp Asp
    130                 135                 140

ttt gtt gag gcc aag gag gcc ggc tac aac gcc cgc ccc gtc ctc gtc       480
Phe Val Glu Ala Lys Glu Ala Gly Tyr Asn Ala Arg Pro Val Leu Val
145                 150                 155                 160

ggt ccc gtc acc ctc ctc gcc ctt ggt aag ccc ggc aag gac gcc aag       528
Gly Pro Val Thr Leu Leu Ala Leu Gly Lys Pro Gly Lys Asp Ala Lys
                165                 170                 175

gac gcc gag ctc gac ccc gtc tcg ctc ctc agc aag ctt gcc ccc gtc       576
Asp Ala Glu Leu Asp Pro Val Ser Leu Leu Ser Lys Leu Ala Pro Val
            180                 185                 190

tac ggt gaa ttg ctc gcc aaa ctc ggc gag gcc ggt gcc gag tgg gtc       624
Tyr Gly Glu Leu Leu Ala Lys Leu Gly Glu Ala Gly Ala Glu Trp Val
        195                 200                 205

cag att gat gag ccc gtc ctc gtt ctt gac cgt gcc cag cag tac gcc       672
Gln Ile Asp Glu Pro Val Leu Val Leu Asp Arg Ala Gln Gln Tyr Ala
    210                 215                 220

gcc gag ttc aag gcc gcc tac gag acc atc gct cag gct gcc ccc tcg       720
Ala Glu Phe Lys Ala Ala Tyr Glu Thr Ile Ala Gln Ala Ala Pro Ser
225                 230                 235                 240

gtc aag atc atg att gct acc tac ttc aac aag ctc gag tcc aac ctc       768
Val Lys Ile Met Ile Ala Thr Tyr Phe Asn Lys Leu Glu Ser Asn Leu
                245                 250                 255

gag atc gtc aag acc ctc ccc gtc gct ggt ctc cac atc gat ctt gac       816
Glu Ile Val Lys Thr Leu Pro Val Ala Gly Leu His Ile Asp Leu Asp
            260                 265                 270

cgt gct cct gag cag ctc gac gag gtc ctc gcc gcc ttc gtt aac acc       864
Arg Ala Pro Glu Gln Leu Asp Glu Val Leu Ala Ala Phe Val Asn Thr
        275                 280                 285

aag cac gtc gtc tcg ctc ggt ctc gtc tcc ggc cgt aac atc tgg aaa       912
Lys His Val Val Ser Leu Gly Leu Val Ser Gly Arg Asn Ile Trp Lys
    290                 295                 300

act gac ctc agc gct gcc ctc aag att gcc cag aag gcc gtc gag aag       960
Thr Asp Leu Ser Ala Ala Leu Lys Ile Ala Gln Lys Ala Val Glu Lys
305                 310                 315                 320

ctc ggc gac gct tcg cgt gtt cag att gct tct tcg tcc tcg ctc ctc      1008
Leu Gly Asp Ala Ser Arg Val Gln Ile Ala Ser Ser Ser Ser Leu Leu
                325                 330                 335

cac acc ccc atc acc atc gcc aac gag aag aag ctg agc gct gag gtg      1056
His Thr Pro Ile Thr Ile Ala Asn Glu Lys Lys Leu Ser Ala Glu Val
            340                 345                 350

ctc gac tgg ttc tcg ttc gcc aac gag aag tgt gct gag att gcc acc      1104
Leu Asp Trp Phe Ser Phe Ala Asn Glu Lys Cys Ala Glu Ile Ala Thr
        355                 360                 365

ctc gct gct gct ctc cgc gac cca agc tcg gcc gcc gac gct ctc gcc      1152
Leu Ala Ala Ala Leu Arg Asp Pro Ser Ser Ala Ala Asp Ala Leu Ala
    370                 375                 380

gtc aac gag aag agc atc aag gcc cgt cgc gac ttt gag aag aac tct      1200
Val Asn Glu Lys Ser Ile Lys Ala Arg Arg Asp Phe Glu Lys Asn Ser
385                 390                 395                 400

gac ccc gcc gtt cgt gaa cgc gtt gcc aac atc aag gag gag gac ctc      1248
Asp Pro Ala Val Arg Glu Arg Val Ala Asn Ile Lys Glu Glu Asp Leu
                405                 410                 415

gcc cgc aag tcg cct ttc aac gtg cga aag gag gtt cag aag gag cac      1296
Ala Arg Lys Ser Pro Phe Asn Val Arg Lys Glu Val Gln Lys Glu His
            420                 425                 430

ctt gcg ctc ccc atc ttc ccc acc acc acc atc ggc tct ttc ccc cag      1344
Leu Ala Leu Pro Ile Phe Pro Thr Thr Thr Ile Gly Ser Phe Pro Gln
        435                 440                 445
```

-continued

```
acc aag gag atc cgt cag tac cgt gcg cgt ttc aac aag tcc gag atc      1392
Thr Lys Glu Ile Arg Gln Tyr Arg Ala Arg Phe Asn Lys Ser Glu Ile
    450                 455                 460

acc aag gag gag tac gaa aag ttc ctc gaa gac gag atc aag atg gtc      1440
Thr Lys Glu Glu Tyr Glu Lys Phe Leu Glu Asp Glu Ile Lys Met Val
465                 470                 475                 480

gtc gag aag cag gag gcc ctc aac ctc gac gtg ctc gtt cac ggt gag      1488
Val Glu Lys Gln Glu Ala Leu Asn Leu Asp Val Leu Val His Gly Glu
                485                 490                 495

ccc gag cgt aac gac atg gtc cag tac ttc ggt gag ctg ctc gac ggt      1536
Pro Glu Arg Asn Asp Met Val Gln Tyr Phe Gly Glu Leu Leu Asp Gly
            500                 505                 510

ttc gtc ttc acc cag aac gcc tgg gtc cag tcg ttc ggt tcg cga tac      1584
Phe Val Phe Thr Gln Asn Ala Trp Val Gln Ser Phe Gly Ser Arg Tyr
        515                 520                 525

gtt cgt ccc ccc gtt gtc gtc tcg gac gtc agc cgt cct gct ccc atg      1632
Val Arg Pro Pro Val Val Val Ser Asp Val Ser Arg Pro Ala Pro Met
    530                 535                 540

act gtg cgc tgg tcg tcg tac gct cag agc ctc acc aag aag ccc atg      1680
Thr Val Arg Trp Ser Ser Tyr Ala Gln Ser Leu Thr Lys Lys Pro Met
545                 550                 555                 560

aag ggt atg ctt act ggt ccc gtc acc atc ctc aac tgg tcg ttc cct      1728
Lys Gly Met Leu Thr Gly Pro Val Thr Ile Leu Asn Trp Ser Phe Pro
                565                 570                 575

cgt gcc gac atc agc aag gag gta cag tcc aag cag atc gcc ctc gcc      1776
Arg Ala Asp Ile Ser Lys Glu Val Gln Ser Lys Gln Ile Ala Leu Ala
            580                 585                 590

ctc cgc gac gag gtc atc gac ctc gag aag gcc ggt gtt cgt gcc gtt      1824
Leu Arg Asp Glu Val Ile Asp Leu Glu Lys Ala Gly Val Arg Ala Val
        595                 600                 605

cag gtc gac gag ccc gcc att cgt gag ggt ctg ccg ctc cgc cag aag      1872
Gln Val Asp Glu Pro Ala Ile Arg Glu Gly Leu Pro Leu Arg Gln Lys
    610                 615                 620

gac tgg gct ggt tac ctg cga tgg gct gtc gac tcg ttc cgt ctc tcc      1920
Asp Trp Ala Gly Tyr Leu Arg Trp Ala Val Asp Ser Phe Arg Leu Ser
625                 630                 635                 640

act tcg ggt tgc tcg gac gcc atg aac atc gcc tcg cac ttc tgc tac      1968
Thr Ser Gly Cys Ser Asp Ala Met Asn Ile Ala Ser His Phe Cys Tyr
                645                 650                 655

tcg gac ttc tcg ctc att atg aag tcg atc atc gag ctc gat gcc gat      2016
Ser Asp Phe Ser Leu Ile Met Lys Ser Ile Ile Glu Leu Asp Ala Asp
            660                 665                 670

atg atc tcg att gag cac tcc aag tcc ggt gag cac ctt ctc ggt gcc      2064
Met Ile Ser Ile Glu His Ser Lys Ser Gly Glu His Leu Leu Gly Ala
        675                 680                 685

ttc aag aag gtt ggc tac ccc tcg cac att ggc cct ggt gtc ttt gac      2112
Phe Lys Lys Val Gly Tyr Pro Ser His Ile Gly Pro Gly Val Phe Asp
    690                 695                 700

atc cac tcg ccc cgt gtg ccc agc aag gac gag atg gtg ggc cgc atc      2160
Ile His Ser Pro Arg Val Pro Ser Lys Asp Glu Met Val Gly Arg Ile
705                 710                 715                 720

aag gcc atg gcc gag gtg ctt ccc aag gac tcg atc tgg gtc aac ccc      2208
Lys Ala Met Ala Glu Val Leu Pro Lys Asp Ser Ile Trp Val Asn Pro
                725                 730                 735

gac tgt ggt ctc aag acc cga acc tgg gag gag tgc act gcc cag ctc      2256
Asp Cys Gly Leu Lys Thr Arg Thr Trp Glu Glu Cys Thr Ala Gln Leu
            740                 745                 750

acc aac atg gtt gct gcc gct gag gag tgc cgc cag acc ctt gct taa      2304
Thr Asn Met Val Ala Ala Ala Glu Glu Cys Arg Gln Thr Leu Ala
        755                 760                 765
```

<210> SEQ ID NO 18
<211> LENGTH: 767
<212> TYPE: PRT
<213> ORGANISM: Ustilago maydis

<400> SEQUENCE: 18

```
Met Ala Thr Ser Ala Val Leu Gly Tyr Pro Arg Ile Gly Pro Gln Arg
1               5                   10                  15

Glu Val Lys Lys Ala Leu Glu Ala Tyr Trp Gly Gly Lys Ser Ser Gln
            20                  25                  30

Glu Glu Leu Leu Lys Val Ala Lys Glu Gln Arg Leu Gln Thr Tyr Lys
        35                  40                  45

Phe Ile Lys Asp Ala Gly Val Asp Val Val Pro Thr Gly Thr Phe Ser
    50                  55                  60

Leu Tyr Asp His Val Leu Asp Ala Ser Asn Thr Phe Asn Leu Ile Pro
65                  70                  75                  80

Glu Asn Tyr Ala Lys Ser Gly Leu Asp Ala Leu Asp Thr Tyr Phe Ala
                85                  90                  95

Met Ala Arg Gly His Gln Lys Asn Gly Val Asp Leu Pro Ala Thr Glu
            100                 105                 110

Met Gln Lys Trp Phe Asp Ser Asn Tyr His Tyr Leu Val Pro Glu Leu
        115                 120                 125

Ser Glu Ser Thr Glu Phe Lys Ile Asn Asn Thr Lys Pro Ile Asp Asp
    130                 135                 140

Phe Val Glu Ala Lys Glu Ala Gly Tyr Asn Ala Arg Pro Val Leu Val
145                 150                 155                 160

Gly Pro Val Thr Leu Leu Ala Leu Gly Lys Pro Gly Lys Asp Ala Lys
                165                 170                 175

Asp Ala Glu Leu Asp Pro Val Ser Leu Leu Ser Lys Leu Ala Pro Val
            180                 185                 190

Tyr Gly Glu Leu Leu Ala Lys Leu Gly Glu Ala Gly Ala Glu Trp Val
        195                 200                 205

Gln Ile Asp Glu Pro Val Leu Val Leu Asp Arg Ala Gln Gln Tyr Ala
    210                 215                 220

Ala Glu Phe Lys Ala Ala Tyr Glu Thr Ile Ala Gln Ala Ala Pro Ser
225                 230                 235                 240

Val Lys Ile Met Ile Ala Thr Tyr Phe Asn Lys Leu Glu Ser Asn Leu
                245                 250                 255

Glu Ile Val Lys Thr Leu Pro Val Ala Gly Leu His Ile Asp Leu Asp
            260                 265                 270

Arg Ala Pro Glu Gln Leu Asp Glu Val Leu Ala Ala Phe Val Asn Thr
        275                 280                 285

Lys His Val Val Ser Leu Gly Leu Val Ser Gly Arg Asn Ile Trp Lys
    290                 295                 300

Thr Asp Leu Ser Ala Ala Leu Lys Ile Ala Gln Lys Ala Val Glu Lys
305                 310                 315                 320

Leu Gly Asp Ala Ser Arg Val Gln Ile Ala Ser Ser Ser Ser Leu Leu
                325                 330                 335

His Thr Pro Ile Thr Ile Ala Asn Glu Lys Lys Leu Ser Ala Glu Val
            340                 345                 350

Leu Asp Trp Phe Ser Phe Ala Asn Glu Lys Cys Ala Glu Ile Ala Thr
        355                 360                 365

Leu Ala Ala Ala Leu Arg Asp Pro Ser Ser Ala Ala Asp Ala Leu Ala
    370                 375                 380
```

-continued

```
Val Asn Glu Lys Ser Ile Lys Ala Arg Arg Asp Phe Glu Lys Asn Ser
385                 390                 395                 400

Asp Pro Ala Val Arg Glu Arg Val Ala Asn Ile Lys Glu Glu Asp Leu
                405                 410                 415

Ala Arg Lys Ser Pro Phe Asn Val Arg Lys Glu Val Gln Lys Glu His
            420                 425                 430

Leu Ala Leu Pro Ile Phe Pro Thr Thr Thr Ile Gly Ser Phe Pro Gln
        435                 440                 445

Thr Lys Glu Ile Arg Gln Tyr Arg Ala Arg Phe Asn Lys Ser Glu Ile
    450                 455                 460

Thr Lys Glu Glu Tyr Glu Lys Phe Leu Glu Asp Glu Ile Lys Met Val
465                 470                 475                 480

Val Glu Lys Gln Glu Ala Leu Asn Leu Asp Val Leu Val His Gly Glu
                485                 490                 495

Pro Glu Arg Asn Asp Met Val Gln Tyr Phe Gly Glu Leu Leu Asp Gly
            500                 505                 510

Phe Val Phe Thr Gln Asn Ala Trp Val Gln Ser Phe Gly Ser Arg Tyr
        515                 520                 525

Val Arg Pro Pro Val Val Val Ser Asp Val Ser Arg Pro Ala Pro Met
    530                 535                 540

Thr Val Arg Trp Ser Ser Tyr Ala Gln Ser Leu Thr Lys Lys Pro Met
545                 550                 555                 560

Lys Gly Met Leu Thr Gly Pro Val Thr Ile Leu Asn Trp Ser Phe Pro
                565                 570                 575

Arg Ala Asp Ile Ser Lys Glu Val Gln Ser Lys Gln Ile Ala Leu Ala
            580                 585                 590

Leu Arg Asp Glu Val Ile Asp Leu Glu Lys Ala Gly Val Arg Ala Val
        595                 600                 605

Gln Val Asp Glu Pro Ala Ile Arg Glu Gly Leu Pro Leu Arg Gln Lys
    610                 615                 620

Asp Trp Ala Gly Tyr Leu Arg Trp Ala Val Asp Ser Phe Arg Leu Ser
625                 630                 635                 640

Thr Ser Gly Cys Ser Asp Ala Met Asn Ile Ala Ser His Phe Cys Tyr
                645                 650                 655

Ser Asp Phe Ser Leu Ile Met Lys Ser Ile Ile Glu Leu Asp Ala Asp
            660                 665                 670

Met Ile Ser Ile Glu His Ser Lys Ser Gly Glu His Leu Leu Gly Ala
        675                 680                 685

Phe Lys Lys Val Gly Tyr Pro Ser His Ile Gly Pro Gly Val Phe Asp
    690                 695                 700

Ile His Ser Pro Arg Val Pro Ser Lys Asp Glu Met Val Gly Arg Ile
705                 710                 715                 720

Lys Ala Met Ala Glu Val Leu Pro Lys Asp Ser Ile Trp Val Asn Pro
                725                 730                 735

Asp Cys Gly Leu Lys Thr Arg Thr Trp Glu Glu Cys Thr Ala Gln Leu
            740                 745                 750

Thr Asn Met Val Ala Ala Ala Glu Glu Cys Arg Gln Thr Leu Ala
        755                 760                 765
```

<210> SEQ ID NO 19
<211> LENGTH: 1003
<212> TYPE: DNA
<213> ORGANISM: Phytophthora infestans
<220> FEATURE:
<221> NAME/KEY: EST
<222> LOCATION: (1)..(1003)

<220> FEATURE:
<221> NAME/KEY: misc_feature
<222> LOCATION: (970)..(970)
<223> OTHER INFORMATION: n is a, c, g, or t

<400> SEQUENCE: 19
cggacgcgtg gkctggcgcg cacttctcaa cgcaagtccg tcccagttca gtaaaccttc 60
tctacacata tatcaagatg gtcgccgtcg acagtgcaac gctgggtttc ccccgcatgg 120
gccccaaccg tgagctcaag ttcgcccttg agaagttctg gcgcaacaag attagcgagg 180
aggagctgta caagattgct aactctgtgg aggaggccaa ctggaagaag cagatcgacg 240
ccggtgtcag ccgtgtgggt gttggcctct tctcgctcta cgaccacgtg ctggactgga 300
cctactactt ggatctggcc ccagagcgct tcgcgtcggt gcccgcmggt ctgtcgcagt 360
acttcgctat ggcccgtggc gttgacggca tccccgctct tgacatgacg aagtggttcg 420
actccaacta ccactacgag gtgcctgagc tcaacgccaa gtccacgccc aaggctaact 480
tcggctcgta tgtggccagc atcaagcgcg ctttggctgt tgtgggcccc aacaagacgg 540
tcccgatcat tctcggccct ctgacttacc tggccctgag caagtacgac ggcgccaccc 600
ttgacgagtt gctggtcaag gtcctgcccc tctacactgc tctgctgaac gagctcgccg 660
gtctaggtgt gcaggaggtg caggtgcacg agccttccct cgttggcact caggccgatc 720
agttggccaa gcaccttgcc accgtctacg gatccaagga ccagaagggt gccattcagc 780
acgagaagct cgccattaac ctggctacat actttgagga gatcaaccac gacgtgtacc 840
agtggtttgc cacgtcgcct gtgtcggcca tctcgcttga ctttacccgc ggtgacaacc 900
tgtcggtgct acagaagttc ggcttccttg ccggcaagcg tctcggtgcc ggtctgatcg 960
acggccctan cgtgtggaag tttcaacccc gacacgatct gtc 1003

<210> SEQ ID NO 20
<211> LENGTH: 308
<212> TYPE: PRT
<213> ORGANISM: Phytophthora infestans
<220> FEATURE:
<221> NAME/KEY: Protein
<222> LOCATION: (1)..(308)

<400> SEQUENCE: 20

Met Val Ala Val Asp Ser Ala Thr Leu Gly Phe Pro Arg Met Gly Pro
1 5 10 15

Asn Arg Glu Leu Lys Phe Ala Leu Glu Lys Phe Trp Arg Asn Lys Ile
20 25 30

Ser Glu Glu Glu Leu Tyr Lys Ile Ala Asn Ser Val Glu Glu Ala Asn
35 40 45

Trp Lys Lys Gln Ile Asp Ala Gly Val Ser Arg Val Gly Val Gly Leu
50 55 60

Phe Ser Leu Tyr Asp His Val Leu Asp Trp Thr Tyr Tyr Leu Asp Leu
65 70 75 80

Ala Pro Glu Arg Phe Ala Ser Val Pro Ala Gly Leu Ser Gln Tyr Phe
85 90 95

Ala Met Ala Arg Gly Val Asp Gly Ile Pro Ala Leu Asp Met Thr Lys
100 105 110

Trp Phe Asp Ser Asn Tyr His Tyr Glu Val Pro Glu Leu Asn Ala Lys
115 120 125

Ser Thr Pro Lys Ala Asn Phe Gly Ser Tyr Val Ala Ser Ile Lys Arg
130 135 140

Ala Leu Ala Val Val Gly Pro Asn Lys Thr Val Pro Ile Ile Leu Gly

-continued

```
145                 150                 155                 160

Pro Leu Thr Tyr Leu Ala Leu Ser Lys Tyr Asp Gly Ala Thr Leu Asp
                165                 170                 175

Glu Leu Leu Val Lys Val Leu Pro Leu Tyr Thr Ala Leu Leu Asn Glu
            180                 185                 190

Leu Ala Gly Leu Gly Val Gln Glu Val Gln Val His Glu Pro Ser Leu
        195                 200                 205

Val Gly Thr Gln Ala Asp Gln Leu Ala Lys His Leu Ala Thr Val Tyr
    210                 215                 220

Gly Ser Lys Asp Gln Lys Gly Ala Ile Gln His Glu Lys Leu Ala Ile
225                 230                 235                 240

Asn Leu Ala Thr Tyr Phe Glu Glu Ile Asn His Asp Val Tyr Gln Trp
                245                 250                 255

Phe Ala Thr Ser Pro Val Ser Ala Ile Ser Leu Asp Phe Thr Arg Gly
            260                 265                 270

Asp Asn Leu Ser Val Leu Gln Lys Phe Gly Phe Leu Ala Gly Lys Arg
        275                 280                 285

Leu Gly Ala Gly Leu Ile Asp Gly Pro Xaa Val Trp Lys Phe Gln Pro
    290                 295                 300

Arg His Asp Leu
305
```